US009936693B2

(12) United States Patent
Tamura et al.

(10) Patent No.: US 9,936,693 B2
(45) Date of Patent: Apr. 10, 2018

(54) EFFICACY-ENHANCING AGENT COMPOSITION FOR AMINO ACID-BASED AGROCHEMICALS

(71) Applicant: KAO CORPORATION, Tokyo (JP)

(72) Inventors: Yoshinori Tamura, Wakayama (JP); Masaki Inoue, Wakayama (JP); Masahiro Mori, Amphur Muang (TH)

(73) Assignee: KAO CORPORATION, Tokyo (JP)

(*) Notice: Subject to any disclaimer, the term of this patent is extended or adjusted under 35 U.S.C. 154(b) by 0 days.

(21) Appl. No.: 15/302,587

(22) PCT Filed: Apr. 6, 2015

(86) PCT No.: PCT/JP2015/060755
§ 371 (c)(1),
(2) Date: Oct. 7, 2016

(87) PCT Pub. No.: WO2015/156256
PCT Pub. Date: Oct. 15, 2015

(65) Prior Publication Data
US 2017/0027170 A1    Feb. 2, 2017

(30) Foreign Application Priority Data
Apr. 9, 2014  (JP) ................. 2014-080214

(51) Int. Cl.
*A01N 25/30* (2006.01)
*A01M 21/04* (2006.01)
*A01N 57/20* (2006.01)
*A01M 21/00* (2006.01)
*A01N 25/00* (2006.01)
*A01N 25/02* (2006.01)
*A01N 37/12* (2006.01)

(52) U.S. Cl.
CPC ............. *A01N 25/30* (2013.01); *A01M 21/00* (2013.01); *A01M 21/043* (2013.01); *A01N 25/00* (2013.01); *A01N 25/02* (2013.01); *A01N 37/12* (2013.01); *A01N 57/20* (2013.01)

(58) Field of Classification Search
USPC ....................................................... 504/206
See application file for complete search history.

(56) References Cited

U.S. PATENT DOCUMENTS

| 2,498,694 | A | 2/1950 | Mast |
| 5,849,663 | A | 12/1998 | Hasebe et al. |
| 5,948,421 | A | 9/1999 | Okano et al. |
| 6,251,220 | B1 | 6/2001 | Irinatsu et al. |
| 6,420,330 | B1* | 7/2002 | Stelter .......... A01N 37/12 510/319 |
| 2004/0115160 | A1 | 6/2004 | Salamone et al. |
| 2010/0016163 | A1* | 1/2010 | Keiper .......... A01N 25/30 504/206 |
| 2011/0229428 | A1 | 9/2011 | Wu et al. |

FOREIGN PATENT DOCUMENTS

| CN | 101121671 A | 2/2008 | |
| CN | 103224753 A | 7/2013 | |
| CN | 103835132 A | 6/2014 | |
| DE | 159263 A3 | 3/1983 | |
| DE | 222893 A1 | 5/1985 | |
| JP | 3-287867 A | 12/1991 | |
| JP | 9-295901 A | 11/1997 | |
| JP | 10-501800 A | 2/1998 | |
| JP | 10-102390 A | 4/1998 | |
| JP | 2000-327544 A | 11/2000 | |
| JP | 2001-159084 A | 6/2001 | |
| JP | 2002-38372 A | 2/2002 | |
| JP | 2004-292405 A | 10/2004 | |
| JP | 2007-56376 A | 3/2007 | |
| JP | 2008-7603 A | 1/2008 | |
| JP | 2010-144310 A | 7/2010 | |
| JP | 2012-201868 A | 10/2012 | |
| JP | 2013-133547 A | 7/2013 | |
| JP | 2014-223617 A | 12/2014 | |
| WO | WO 2012/081093 A1 | 5/2012 | |
| WO | WO 2012061093 A1 * | 5/2012 | ........... C07C 6/04 |

OTHER PUBLICATIONS

Extended European Search Report, dated Jan. 16, 2018, for European Application No. 15777257.5.
Geng et al., "Process for synthesis of ester amine and its quaternary ammonium salts," Database CA [Online], STN Database Accession No. 2008:208485, Feb. 13, 2008, XP002776873, pp. 1-3.
Gorodnov et al., "Cation-active demulsifiers from fatty acids," Database CA [Online], STN Database Accession No. 1974:537846, 1974, XP002776883, pp. 1-2.
Huang et al., "A biodegradable antistatic finishing agent and its preparation method," Database CA [Online], STN Database Accession No. 2014:922885, Jun. 4, 2014, XP002776868, pp. 1-3.
Inamasu et al., "Hair cosmetic compositions containing ester cationic surfactants," Database CA [Online], STN Database Accession No. 2004:876460, Oct. 21, 2004, XP002776876, pp. 1-2.
Irinatsu et al., "Agents and method for deinking of recycled paper by the floatation process," Database CA [Online], STN Database Accession No. 1998:242126, Apr. 21, 1998, XP002776880, pp. 1-2.
Johnston, "Magnesium in Canadian crop production," Database CA [Online], STN Database Accession No. 1949:52143, 1949, XP002776884, 1 page.
Kawasaki et al., "Water-dispersible storage-stable fabric softening agent compositions," Database CA [Online], STN Database Accession No. 2002:98926, Feb. 6, 2002, XP002776877, pp. 1-2.
Kim et al., "Manufacture of oil-in-water emulsions containing capsule particles," Database CA [Online], STN Database Accession No. 2014:2010790, Dec. 4, 2014, XP002776867, pp. 1-4.
Kondo et al., "Cationic surfactant-coated silica compositions as additive for solvent-based coatings," Database CA [Online], STN Database Accession No. 2012:1533644, Oct. 22, 2012, XP002776871, pp. 1-2.

(Continued)

*Primary Examiner* — Johann R Richter
*Assistant Examiner* — Courtney A Brown
(74) *Attorney, Agent, or Firm* — Birch, Stewart, Kolasch & Birch, LLP

(57) ABSTRACT

The present invention is an efficacy-enhancing agent composition for amino acid-based agrochemicals, which contains 3 kinds of specific quaternary ammonium salts having an ester group in a specific mass ratio.

10 Claims, No Drawings

(56) References Cited

OTHER PUBLICATIONS

Nie et al., "Photocurable antifogging coating material and photocurable quaternary ammonium salt therefor," Database CA [Online], STN Database Accession No. 2013:1197260, Jul. 31, 2013, XP002776869, pp. 1-2.

Shindo et al., "Liquid bleach products with good applicability and liquid bleach compositions with good detergency against mud soil," Database CA [Online], STN Database Accession No. 2008:63985, Jan. 17, 2008, XP002776874, pp. 1-2.

Shirado et al., "Silicon compound textile treatment compositions and method for suppressing hydrolysis of the silicon compounds," Database CA [Online], STN Database Accession No. 2010:815019, Jul. 1, 2010, XP002776872, pp. 1-3.

Tanemura et al., "Storage-stable hair rinses containing cationic surfactants," Database CA [Online], STN Database Accession No. 2000:830116, Nov. 28, 2000, XP002776879, pp. 1-2.

Ushio et al., "Softening agent emulsion-filled bags," Database CA [Online], STN Database Accession No. 2013:1053189, Jul. 8, 2013, XP002776870, pp. 1-4.

Yamamoto et al., "(Semi)transparent liquid fabric softeners," Database CA [Online], STN Database Accession No. 2007:254325, Mar. 8, 2007, XP002776875, pp. 1-2.

Yamamura et al., "Softening agents for imparting improved resilience to fabrics," Database CA [Online], STN Database Accession No. 1992:237829, Dec. 18, 1991, XP002776881, pp. 1-2.

Yoshiuchi et al., "Removers for hot melt adhesives and regeneration of pulp from wastepaper," Database CA [Online], STN Database Accession No. 2001:423501, Jun. 12, 2001, XP002776878, pp. 1-2.

Zhurovska et al., "Effect of some structural elements of antistatic agents on the electric conductivity of synthetic fibers modified with them," Database CA [Online], STN Database Accession No. 1978:154240, XP002776882, pp. 1-3.

International Search Report for PCT/JP2015/060755 dated Jul. 7, 2015.

\* cited by examiner

US 9,936,693 B2

1

EFFICACY-ENHANCING AGENT COMPOSITION FOR AMINO ACID-BASED AGROCHEMICALS

FIELD OF THE INVENTION

The present invention relates to an efficacy-enhancing agent composition for amino acid-based agrochemicals, an agrochemical composition, and a method for weeding.

BACKGROUND OF THE INVENTION

Conventionally, in order to fully bring out the effects of agrochemicals, various surfactants have been used for agrochemical-containing compositions. It is known that: for amino acid-based agrochemicals like a glyphosate salt, which is one of active ingredients most often used particularly as a herbicide, application of a nonionic surfactant or an anionic surfactant commonly used for other agrochemicals is difficult in terms of the compatibility; instead, quaternized or polyoxyethylenated long-chain amines are effective for this purpose. Among amino acid-based agrochemicals such as glyphosate salts, particularly a polyoxyethylenated tallowamine is widely used due to its excellent cost performance. However, since a polyoxyethylenated tallowamine has a very low biodegradability and a strong fish toxicity, its impact on the environment has been a concern in recent years, and a substitute is desired. Thus, JP-A 10-501800, for example, proposes a quaternary salt modified with polyoxyalkylene as an agrochemical efficacy-enhancing agent.

JP-A 9-295901 discloses a liquid agrochemical composition, which contains a water-soluble agrochemical active ingredient, a specific amine compound having an alkylene oxide chain or an acid salt or quaternized product thereof, and a specific amine compound or quaternized compound; and describes a glyphosate salt as the water-soluble agrochemical active ingredient.

SUMMARY OF THE INVENTION

The present invention relates to an efficacy-enhancing agent composition for amino acid-based agrochemicals, comprising a compound (A1) represented by the following general formula (1-1), optionally a compound (A2) represented by the following general formula (1-2), and optionally a compound (A3) represented by the following general formula (1-3), wherein:

the mass ratio of the content of the compound (A3) to the sum of the contents of the compound (A1) and the compound (A2), [content of compound (A3)]/[sum of contents of compounds (A1) and (A2)], is 0/100 or more and 10/90 or less; and the mass ratio of the content of the compound (A2) to the content of the compound (A1), [content of compound (A2)]/[content of compound (A1)], is 0/100 or more and 50/50 or less.

[Chemical Formula 1]

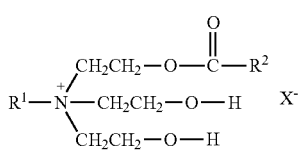

(1-1)

2

-continued

[Chemical Formula 2]

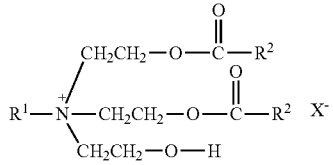

(1-2)

[Chemical Formula 3]

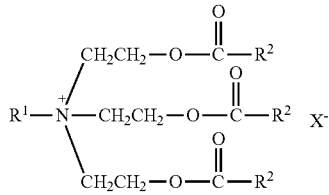

(1-3)

In the formulas, $R^1$ denotes a linear alkyl group having 1 or more and 4 or less carbon atoms, a linear alkenyl group having 2 or more and 4 or less carbon atoms, a branched alkyl group having 3 or more and 4 or less carbon atoms, or a branched alkenyl group having 3 or more and 4 or less carbon atoms; $R^2$ denotes a linear or branched alkyl or alkenyl group having 5 or more and 11 or less carbon atoms; and $X^-$ denotes a counter ion.

Further, the present invention relates to an agrochemical composition, which contains the efficacy-enhancing agent composition for amino acid-based agrochemicals of the present invention, an amino acid-based agrochemical active ingredient (D), and water.

Further, the present invention relates to a weeding method, which includes spraying an agrochemical spray solution prepared from the agrochemical composition of the present invention on plants.

DETAILED DESCRIPTION OF THE INVENTION

According to the present invention, there are provided an efficacy-enhancing agent composition for amino acid-based agrochemicals, which is excellent in the biodegradability and the aquatic organism toxicity (fish toxicity), excellent in the compatibility with amino acid-based agrochemicals, and stable, and which can effectively enhance efficacies of amino acid-based agrochemicals, especially rain resistance; and an agrochemical composition containing the same.

Further, use of the agrochemical composition of the present invention can provide a weeding method having an excellent weeding effect.

The efficacy-enhancing agent composition for agrochemicals of the present invention enhances the rain resistance of amino acid-based agrochemicals. That is, when the efficacy-enhancing agent composition for agrochemicals of the present invention is used with an amino acid-based agrochemical, the effects of the amino acid-based agrochemical are not reduced even when a rainfall occurs within a short time period after being sprayed on plants. This is considered to be that the efficacy-enhancing agent composition for agrochemicals of the present invention enhances the penetration of amino acid-based agrochemicals into plants and the movement inside plants.

The efficacy-enhancing agent composition for agrochemicals of the present invention with an excellent effect of enhancing the rain resistance can produce effects such as an extension of an interval of spraying of an amino acid-based agrochemical, a reduction in a spraying amount thereof, and avoidance of weeding effect dissipation caused by rainfall or the like after spraying of amino acid-based agrochemicals.

JP-A 10-501800 or JP-A 9-295901 is not satisfactory in terms of effectively enhancing effects of agrochemicals.

The present invention provides an efficacy-enhancing agent composition for amino acid-based agrochemicals, which is excellent in the biodegradability and the aquatic organism toxicity (fish toxicity), excellent in the compatibility with amino acid-based agrochemicals, and stable, and which can effectively enhance efficacies of amino acid-based agrochemicals, especially rain resistance; an agrochemical composition containing the same; and a weeding method using the agrochemical composition.

The present inventors made intensive researches on techniques, which, in an agrochemical formulation containing an amino acid-based agrochemical such as a glyphosate salt, can provide a stable agrochemical formulation excellent in the biodegradability and the fish toxicity and excellent in the cost performance, and further can develop a high weeding performance. Then, they have found that combination of a cationic compound with a specific structure in a specific ratio can excel in the biodegradability and the fish toxicity and can effectively enhance efficacies of amino acid-based agrochemicals, especially rain resistance; further, when a specific compound and a specific nonionic surfactant are blended in a certain ratio, more stable efficacy-enhancing agent composition for amino acid-based agrochemicals and agrochemical composition are obtained, thereby completing the present invention.

Hereinafter, the present invention will be explained in detail.

<Efficacy-Enhancing Agent Composition for Amino Acid-Based Agrochemicals>

An efficacy-enhancing agent composition for amino acid-based agrochemicals of the present invention contains a compound (A1) represented by the above general formula (1-1).

In the general formula (1-1), $R^1$ is a linear alkyl group with 1 or more and 4 or less carbon atoms, a linear alkenyl group with 2 or more and 4 or less carbon atoms, a branched alkyl group with 3 or more and 4 or less carbon atoms, or a branched alkenyl group with 3 or more and 4 or less carbon atoms. From the viewpoint of enhancing efficacies of agrochemicals, especially rain resistance, and the viewpoint of excellent formulation stability of agrochemical compositions, $R^1$ is preferably a linear group. Further, from the viewpoint of enhancing efficacies of agrochemicals, especially rain resistance, and the viewpoint of excellent formulation stability of agrochemical compositions, $R^1$ has a carbon number of preferably 1 or more and 3 or less, more preferably 1 or more and 2 or less, and further preferably 1. Considering the above viewpoints together, $R^1$ is preferably a linear alkyl group with 1 or more and 4 or less carbon atoms, more preferably a linear alkyl group with 1 or more and 3 or less carbon atoms, further preferably a linear alkyl group with 1 or more and 2 or less carbon atoms, and further more preferably a linear alkyl group with 1 carbon atom.

Further, in the general formula (1-1), $R^2$ is a linear or branched alkyl or alkenyl group with 5 or more and 11 or less carbon atoms. From the viewpoint of enhancing efficacies of agrochemicals, especially rain resistance, and the viewpoint of excellent formulation stability of agrochemical compositions, $R^2$ is preferably a linear group. Further, from the viewpoint of enhancing efficacies of agrochemicals, especially rain resistance, and the viewpoint of excellent formulation stability of agrochemical compositions, $R^2$ is preferably an alkyl group. Furthermore, from the viewpoint of enhancing efficacies of agrochemicals, especially rain resistance, and the viewpoint of excellent formulation stability of agrochemical compositions, $R^2$ has a carbon number of preferably 7 or more and 11 or less, more preferably 7 or more and 9 or less, and further preferably 9. Considering the above viewpoints together, $R^2$ is preferably a linear or branched alkyl or alkenyl group with 7 or more and 11 or less carbon atoms, more preferably a linear or branched alkyl group with 7 or more and 11 or less carbon atoms, preferably a linear alkyl group with 7 or more and 11 or less carbon atoms, more preferably a linear alkyl group with 7 or more and 9 or less carbon atoms, and further preferably a linear alkyl group with 9 carbon atoms.

In the general formula (1-1), $X^-$ is a counter ion and examples thereof include halogenide ions such as $Cl^-$, $Br^-$ and $I^-$, and anions such as alkyl sulfate anions, alkylbenzenesulfonate anions and fatty acid anions. From the viewpoint of enhancing efficacies of agrochemicals, especially rain resistance, and the viewpoint of excellent formulation stability of agrochemical compositions, $X^-$ is preferably a halogenide ion or an alkyl sulfate anion, more preferably an alkyl sulfate anion, more preferably a methyl sulfate anion or an ethyl sulfate anion, and further more preferably a methyl sulfate anion.

From the viewpoint of enhancing efficacies of agrochemicals, especially rain resistance, and the viewpoint of excellent formulation stability of agrochemical compositions, the efficacy-enhancing agent composition for amino acid-based agrochemicals of the present invention contains the compound (A1) in an amount of preferably 25% by mass or more, further preferably 27% by mass or more, further more preferably 30% by mass or more, and further more preferably 33% by mass or more; and, from the viewpoint of the economic efficiency, preferably 60% by mass or less, more preferably 50% by mass or less, and more preferably 40% by mass or less.

Further, the compound (A1) represented by the general formula (1-1) can be obtained by, for example, esterifying triethanolamine through reaction with a fatty acid satisfying the carbon number conditions for $R^2$ and further quaternizing. Further, the compound (A1) can be obtained by mixing triethanolamine with a suitable fat and oil having a fatty acid moiety satisfying the carbon number conditions for $R^2$ in an arbitrary ratio, causing transesterification reaction, and then quaternizing. Usually, these methods produce a reaction product as a mixture, which contains, other than the compound (A1), a compound (A2) represented by the following general formula (1-2) and a compound (A3) represented by the following general formula (1-3), and further, as a mixture, which contains a compound (A4) represented by the following general formula (1-4). In such mixture, ratios of the compound (A2), the compound (A3) and the compound (A4) to the compound (A1) can be adjusted by a molar ratio between triethanolamine and the fatty acid, a molar ratio between the fat and oil and triethanolamine, a reaction temperature, and a reaction period. In general, when the molar ratio of the fatty acid or the fat and oil to triethanolamine is smaller, the ratio of the compound (A1) in such mixture tends to be higher. Examples of a method for enhancing the ratio of the compound (A1) in such mixture include a method wherein the molar ratio of fatty acid to triethanolamine is preferably 0.3/1 or more and 1.1/1 or less, more preferably 0.4/1 or more and 1/1 or less, further preferably 0.4/1 or more and 0.8/1 or less, and further more preferably 0.5/1 or more and 0.7/1 or less. In using a fat and oil, adjustment may be made so that the fatty acid moiety satisfies the above molar ratios. From the viewpoint of balancing the effects and the economic efficiency, a mixture containing the compound (A1) and further at least one compound selected from the compounds (A2), (A3) and (A4) may be used for the preparation of the efficacy-enhancing agent composition for amino acid-based agrochemicals of the present invention. Therefore, the efficacy-enhancing agent composition for amino acid-based agrochemicals of the present invention contains the compound (A1) represented by the above general formula (1-1), and further, at least one compound selected from the compound (A2) represented by the following general formula (1-2), the compound (A3) represented by the following general formula (1-3) and the compound (A4) represented by the following general formula (1-4). However, the mass ratio of [content of compound (A3)]/[sum of content of compound (A1) and content of compound (A2)]; and the mass ratio of [content of compound (A2)]/[content of compound (A1)] have to be within predetermined ranges of the present invention.

Hereinafter, the compounds (A1), (A2), (A3) and (A4) are sometimes mentioned collectively as compound (A).

The compound (A) contains at least the compound (A1). The efficacy-enhancing agent composition for amino acid-based agrochemicals of the present invention may contain one or more kinds of the compound (A2), the compound (A3) and the compound (A4), respectively.

[Chemical Formula 4]

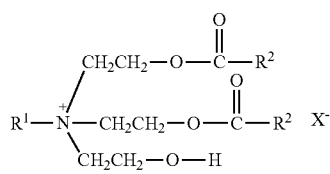

(1-2)

[Chemical Formula 5]

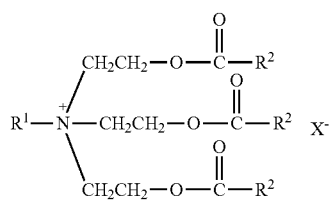

(1-3)

[Chemical Formula 6]

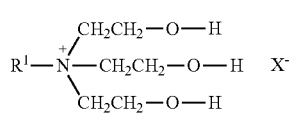

(1-4)

[In the general formulas (1-2), (1-3) and (1-4), $R^1$ denotes a linear alkyl group having 1 or more and 4 or less carbon atoms, a linear alkenyl group having 2 or more and 4 or less carbon atoms, a branched alkyl group having 3 or more and 4 or less carbon atoms, or a branched alkenyl group having 3 or more and 4 or less carbon atoms;

$R^2$ denotes a linear or branched alkyl or alkenyl group having 5 or more and 11 or less carbon atoms; and $X^-$ denotes a counter ion.]

In the general formulas (1-2), (1-3) and (1-4), $R^1$ is preferably the same as $R^1$ of the general formula (1-1).

Further, in the general formulas (1-2) and (1-3), $R^2$ is preferably the same as $R^2$ of the general formula (1-1). It should be noted that in the general formulas (1-2) and (1-3), $R^2$s in these formulas may be the same or different.

Furthermore, in the general formulas (1-2), (1-3) and (1-4), $X^-$ is a counter ion, and $X^-$ is preferably the same as $X^-$ of the general formula (1-1).

In the efficacy-enhancing agent composition for amino acid-based agrochemicals of the present invention, from the viewpoint of enhancing efficacies of agrochemicals, especially rain resistance, and the viewpoint of excellent formulation stability of agrochemical compositions and from the viewpoint of the economic efficiency, the mass ratio of the content of the compound (A3) to the sum of the content of the compound (A1) and the content of the compound (A2), [content of compound (A3)]/[sum of contents of compounds (A1) and (A2)], is 0/100 or more and 10/90 or less. The mass ratio of [content of compound (A3)]/[sum of contents of compounds (A1) and (A2)] is, from the viewpoint of the economic efficiency, preferably 1/99 or more, more preferably 2/98 or more, further preferably 3/97 or more, and further more preferably 4/96; and, from the viewpoint of enhancing efficacies of agrochemicals, especially rain resistance, and the viewpoint of excellent formulation stability of agrochemical compositions, preferably 9/91 or less, more preferably 7/93 or less, further preferably 6/94 or less, and further more preferably 5/95 or less.

In the efficacy-enhancing agent composition for amino acid-based agrochemicals of the present invention, from the viewpoint of enhancing efficacies of agrochemicals, especially rain resistance, and the viewpoint of excellent formulation stability of agrochemical compositions, and from the viewpoint of the economic efficiency, the mass ratio of the content of the compound (A2) to the content of the compound (A1), [content of compound (A2)/content of compound (A1)], is 0/100 or more and 50/50 or less. The mass ratio of [content of compound (A2)/content of compound (A1)] is, from the viewpoint of the economic efficiency, preferably 5/95 or more, more preferably 15/85 or more, further preferably 20/80 or more, further more preferably 25/75 or more, and further more preferably 28/72 or more; and, from the viewpoint of enhancing efficacies of agrochemicals, especially rain resistance, and the viewpoint of excellent formulation stability of agrochemical compositions, preferably 46/54 or less, more preferably 44/54 or less, further preferably 40/60 or less, further more preferably 37/63 or less, and further more preferably 30/70 or less.

The efficacy-enhancing agent composition for amino acid-based agrochemicals of the present invention may contain the compound (A2) within such a range that the effects of the present invention are not deteriorated. The efficacy-enhancing agent composition for amino acid-based agrochemicals of the present invention contains the compound (A2), from the viewpoint of balancing the effects and the economic efficiency, in an amount of 1% by mass or more, more preferably 5% by mass or more, further preferably 10% by mass or more; and, from the viewpoint of not deteriorating the effects of the present invention, preferably 25% by mass or less, more preferably 23% by mass or less, further preferably 19% by mass or less, and further more preferably 15% by mass or less.

The efficacy-enhancing agent composition for amino acid-based agrochemicals of the present invention may contain the compound (A3) within such a range that the effects of the present invention are not deteriorated. The efficacy-enhancing agent composition for amino acid-based agrochemicals of the present invention contains the compound (A3), from the viewpoint of balancing the effects and the economic efficiency, in an amount of preferably 0.5% by mass or more, more preferably 1.0% by mass of more, and further preferably 1.3% by mass or more; and, from the viewpoint of not deteriorating the effects of the present invention, preferably 6% by mass or less, more preferably 5.3% by mass or less, further preferably 4% by mass or less, further more preferably 3.3% by mass or less, further more preferably 2.2% by mass or less, and further more preferably 2.0% by mass or less.

The efficacy-enhancing agent composition for amino acid-based agrochemicals of the present invention may contain the compound (A4) within such a range that the effects of the present invention are not deteriorated. The efficacy-enhancing agent composition for amino acid-based agrochemicals of the present invention contains the compound (A4), from the viewpoint of balancing the effects and the economic efficiency, in an amount of preferably 1% by mass or more, more preferably 5% by mass or more, further preferably 10% by mass or more, and further more preferably 15% by mass or more; and preferably 25% by mass or less, more preferably 20% by mass or less, and further preferably 18% by mass or less.

In the efficacy-enhancing agent composition for amino acid-based agrochemicals of the present invention, from the viewpoint of enhancing efficacies of agrochemicals, especially rain resistance, and the viewpoint of excellent formulation stability of agrochemical compositions and from the viewpoint of the economic efficiency, the mass ratio of the content of the compound (A4) to the sum of the content of the compound (A1) and the content of the compound (A2), [content of compound (A4)]/[sum of contents of compounds (A1) and (A2)], is preferably 0/100 or more and 50/50 or less. The mass ratio of [content of compound (A4)]/[sum of contents of compounds (A1) and (A2)] is, from the viewpoint of the economic efficiency, preferably 10/90 or more, more preferably 12/88 or more, further preferably 15/85 or more, further more preferably 20/80 or more, and further more preferably 24/76 or more; and, from the viewpoint of enhancing efficacies of agrochemicals, especially rain resistance, and the viewpoint of excellent formulation stability of agrochemical compositions, preferably 40/60 or less, more preferably 35/65 or less and further preferably 30/70 or less.

In the present invention, the ratio of the compound (A1) in the total of the contents of the compounds (A1) (A2), (A3) and (A4) is, from the viewpoint of enhancing efficacies of agrochemicals, especially rain resistance, and the viewpoint of excellent formulation stability of agrochemical compositions, preferably 40% by mass or more, more preferably 42% by mass or more, further preferably 45% by mass or more, further more preferably 48% by mass or more, and further more preferably 50% by mass or more; and, from the viewpoint of the economic efficiency, 100% by mass or less, preferably 80% by mass or less, more preferably 70% by mass or less, and further preferably 60% by mass or less.

As an example of the present invention, there is provided an efficacy-enhancing agent composition for amino acid-based agrochemicals, which contains the compound (A1) optionally the compound (A2), optionally the compound (A3) and optionally the compound (A4), wherein:

the mass ratio of the content of the compound (A3) to the sum of the content of the compound (A1) and the content of the compound (A2), [content of compound (A3)]/[sum of contents of compounds (A1) and (A2)], is 0/100 or more and 10/90 or less;

the mass ratio of the content of the compound (A2) to the content of the compound (A1), [content of compound (A2)]/[content of compound (A1)], is 0/100 or more and 50/50 or less; and the mass ratio of the content of the compound (A4) to the sum of the content of the compound (A1) and the content of the compound (A2), [content of compound (A4)]/[sum of contents of compounds (A1) and (A2)], is 0/100 or more and 50/50 or less.

Further, as an example of the present invention, there is provided an efficacy-enhancing agent composition for amino acid-based agrochemicals, which contains the compound (A1), and at least one compound selected from the compounds (A2), (A3) and (A4), wherein:

the mass ratio of the content of the compound (A3) to the sum of the content of the compound (A1) and the content of the compound (A2), [content of compound (A3)]/[sum of contents of compounds (A1) and (A2)], is 0/100 or more and 10/90 or less; and the mass ratio of the content of the compound (A2) to the content of the compound (A1), [content of compound (A2)]/[content of compound (A1)], is 0/100 or more and 50/50 or less.

Further, as an example of the present invention, there is provided an efficacy-enhancing agent composition for amino acid-based agrochemicals, which contains the compounds (A1), (A2), (A3) and (A4), wherein:

the mass ratio of the content of the compound (A3) to the sum of the content of the compound (A1) and the content of the compound (A2), [content of compound (A3)]/[sum of contents of compounds (A1) and (A2)], is 1/99 or more and 10/90 or less; and the mass ratio of the content of the compound (A2) to the content of the compound (A1), [content of compound (A2)]/[content of compound (A1)], is 5/95 or more and 50/50 or less.

Further, as an example of the present invention, there is provided an efficacy-enhancing agent composition for amino acid-based agrochemicals, which contains the compound (A1), the compound (A2), the compound (A3) and the compound (A4), wherein:

the mass ratio of the content of the compound (A3) to the sum of the content of the compound (A1) and the content of the compound (A2), [content of compound (A3)]/[sum of contents of compounds (A1) and (A2)], is 1/99 or more and 10/90 or less;

the mass ratio of the content of the compound (A2) to the content of the compound (A1), [content of compound (A2)]/[content of compound (A1)], is 5/95 or more and 50/50 or less; and the mass ratio of the content of the compound (A4) to the sum of the content of the compound (A1) and the content of the compound (A2), [content of compound (A4)]/[sum of contents of compounds (A1) and (A2)], is 10/90 or more and 50/50 or less.

Further, as an example of the present invention, there is provided an efficacy-enhancing agent composition for amino acid-based agrochemicals, which contains a quaternized product of a reaction product between triethanolamine and a fatty acid with 6 or more and 12 or less carbon atoms.

Further, as an example of the present invention, there is provided an efficacy-enhancing agent composition for amino acid-based agrochemicals, which contains a quaternized product of a reaction product between triethanolamine and a fatty acid with 6 or more and 12 or less carbon atoms, wherein the quaternized product contains the compound (A1)

Further, as an example of the present invention, there is provided an efficacy-enhancing agent composition for amino acid-based agrochemicals, which contains a quaternized product of a reaction product between triethanolamine and a fatty acid with 6 or more and 12 or less carbon atoms, wherein:

the quaternized product contains the compounds (A1), (A2), (A3) and (A4);

the mass ratio of the content of the compound (A3) to the sum of the content of the compound (A1) and the content of the compound (A2), [content of compound (A3)]/[sum of contents of compounds (A1) and (A2)], is 1/99 or more and 10/90 or less; and the mass ratio of the content of the compound (A2) to the content of the compound (A1), [content of compound (A2)]/[content of compound (A1)], is 5/95 or more and 50/50 or less.

In these examples, the above-described preferred matters are applicable, and the below-described compound (B) or the compound (C) may be contained.

From the viewpoint of enhancing efficacies of agrochemicals, especially rain resistance, the efficacy-enhancing agent composition for amino acid-based agrochemicals of the present invention preferably further contains at least one compound (B) selected from compounds represented by the following general formula (B1).

(B1)

[In the general formula (B1),
$R^{1b}$ denotes a linear or branched alkyl or alkenyl group with 10 or more and 16 or less carbon atoms;
EO denotes an ethyleneoxy group;
l denotes an average addition molar number of ethyleneoxy group and is a number of 3 or more and 40 or less; and
$R^{2b}$ denotes a hydrogen atom or a methyl group.]

In the general formula (B1), $R^{1b}$ is, from the viewpoint of enhancing efficacies of agrochemicals, especially rain resistance, a linear or branched alkyl or alkenyl group with 10 or more and 16 or less carbon atoms, preferably a linear or branched alkyl or alkenyl group with 10 or more and 14 or less carbon atoms, more preferably a linear or branched alkyl or alkenyl group with 10 or more and 12 or less carbon atoms, further preferably a linear or branched alkyl or alkenyl group with 12 carbon atoms, and further more preferably a linear alkyl group with 12 carbon atoms. Further, l denotes an average addition molar number of ethyleneoxy group (EO), and from the viewpoint of enhancing efficacies of agrochemicals, especially rain resistance, it is 3 or more, preferably 4 or more, more preferably 5 or more, and further preferably 6; and 40 or less, preferably 30 or less, more preferably 20 or less, further preferably 10 or less, and further more preferably 8 or less. Further, $R^{2b}$ is, from the viewpoint of enhancing efficacies of agrochemicals, especially rain resistance, a hydrogen atom or a methyl group, preferably a hydrogen atom.

From the viewpoint of enhancing efficacies of agrochemicals, especially rain resistance, the efficacy-enhancing agent composition for amino acid-based agrochemicals of the present invention contains the compound (B) in an amount of preferably 2% by mass or more, more preferably 4% by mass or more, further preferably 5% by mass or more, further more preferably 8% by mass or more, and further more preferably 10% by mass or more; and preferably 20% by mass or less, more preferably 15% by mass or less, and further preferably 12% by mass or less.

From the viewpoint of enhancing efficacies of agrochemicals, especially rain resistance, the efficacy-enhancing agent composition for amino acid-based agrochemicals of the present invention preferably further contains at least one compound (C) selected from compounds (C1) represented by the general formula (C1) and compounds (C2) represented by the general formula (C2). It is more preferable to contain, as the compound (C), at least one compound selected from the compounds (C1).

(C1)

[In the general formula (C1),
$R^{1c}$ denotes a linear or branched alkyl or alkenyl group with 6 or more and 12 or less carbon atoms;
PO denotes a propyleneoxy group;
EO denotes an ethyleneoxy group;
m denotes an average addition molar number of propyleneoxy group and is a number of 1 or more and 25 or less;
n denotes an average addition molar number of ethyleneoxy group and is a number of 0 or more and 4 or less; and
$R^{2c}$ denotes a hydrogen atom or a methyl group.
The sign "/" means that PO and EO are bonded in a random form or a block form.]

(C2)

[In the general formula (C2),
$R^{3c}$ denotes a linear or branched alkyl group with 8 or more and 14 or less carbon atoms.]

In the general formula (C1), $R^{1c}$ is, from the viewpoint of enhancing efficacies of agrochemicals, especially rain resistance, a linear or branched alkyl or alkenyl group with 6 or more and 12 or less carbon atoms, preferably a linear or branched alkyl or alkenyl group with 8 or more and 12 or less carbon atoms, more preferably a linear or branched alkyl or alkenyl group with 8 or more and 10 or less, further preferably a linear alkyl group with 8 or more and 10 or less carbon atoms, and further more preferably a linear alkyl group with 8 carbon atoms. Further, m denotes an average addition molar number of propyleneoxy group (PO), and from the viewpoint of enhancing efficacies of agrochemicals, especially rain resistance, it is 1 or more, preferably 2 or more, and more preferably 3 or more; and 25 or less, preferably 10 or less, more preferably 5 or less, further preferably 4 or less, and further more preferably 3. Further, n denotes an average addition molar number of ethyleneoxy group (EO), and from the viewpoint of enhancing efficacies of agrochemicals, especially rain resistance, it is 0 or more; and 4 or less, preferably 3 or less, more preferably 2 or less, more preferably 1 or less and more preferably 0. Further, in the compound (C), from the viewpoint of enhancing efficacies of agrochemicals, especially rain resistance, the ratio of m to the total of m and n, m/(m+n), in the general formula (C1) is preferably 0.5 or more, more preferably 0.6 or more, more preferably 0.7 or more, more preferably 0.8 or more, more preferably 0.9 or more; and preferably 1.0 or less, and preferably 1.0. Further, $R^{2c}$ is from the viewpoint of enhancing efficacies of agrochemicals, especially rain resistance, a hydrogen atom or a methyl group, preferably a hydrogen atom. Further, when PO and EO coexist in the compound (C1), PO and EO are preferably bonded in a block form from the viewpoint of enhancing efficacies of agrochemicals, especially rain resistance, and bonded to $R^{1c}O—$ in the block form further preferably in order of $(PO)_m$ and $(EO)_n$.

In the general formula (C2), $R^{3c}$ is, from the viewpoint of enhancing efficacies of agrochemicals, especially rain resistance, preferably a linear or branched alkyl group with 8 or more and 12 or less carbon atoms, preferably a linear or branched alkyl group with 8 or more and 10 or less carbon atoms, more preferably a linear alkyl group with 8 or more and 10 or less carbon atoms, and further preferably a linear alkyl group with 10 carbon atoms.

From the viewpoint of enhancing efficacies of agrochemicals, especially rain resistance, the efficacy-enhancing agent composition for amino acid-based agrochemicals of the present invention contains the compound (C) in an amount of preferably 2% by mass or more, more preferably 4% by mass or more, further preferably 5% by mass or more, further more preferably 8% by mass or more, and further more preferably 10% by mass or more; and preferably 20% by mass or less, more preferably 15% by mass or less, and further preferably 12% by mass or less.

When the efficacy-enhancing agent composition for amino acid-based agrochemicals of the present invention contains the compound (B), the mass ratio of the content of the compound (A1) to the content of the compound (B), [content of compound (A1)]/[content of compound (B)], is, from the viewpoint of enhancing efficacies of agrochemicals, especially rain resistance, and the viewpoint of excellent formulation stability of agrochemical compositions, preferably 1.5/1 or more, more preferably 2/1 or more, and further preferably 2.5/1 or more; and preferably 10/1 or less, more preferably 7/1 or less, further preferably 5.5/1 or less, further more preferably 4/1 or less, and further more preferably 3/1 or less.

When the efficacy-enhancing agent composition for amino acid-based agrochemicals of the present invention contains the compound (C), the mass ratio of the content of the compound (A1) to the content of the compound (C), [content of compound (A1)]/[content of compound (C)], is, from the viewpoint of enhancing efficacies of agrochemicals, especially rain resistance, preferably 1.5/1 or more, more preferably 2/1 or more, further preferably 2.5/1 or more; and preferably 10/1 or less, more preferably 7/1 or less, more preferably 5.5/1 or less, further more preferably 4/1 or less, and further more preferably 3/1 or less.

When the efficacy-enhancing agent composition for amino acid-based agrochemicals of the present invention contains the compound (B) and the compound (C), the mass ratio of the content of the compound (A1) to the sum of the content of the compound (B) and the content of the compound (C), [content of compound (A1)]/[sum of contents of compound (B) and compound (C)], is, from the viewpoint of enhancing efficacies of agrochemicals, especially rain resistance, and the viewpoint of excellent formulation stability of agrochemical compositions, preferably 1.5/1 or more, more preferably 2/1 or more, and further preferably 2.5/1 or more; and preferably 7/1 or less, more preferably 5.5/1 or less, further preferably 4/1 or less, and further more preferably 3/1 or less.

When the efficacy-enhancing agent composition for amino acid-based agrochemicals of the present invention contains the compound (B) and the compound (C), the mass ratio of the content of the compound (B) to the content of the compound (C), [content of compound (B)]/[content of compound (C)], is, from the viewpoint of enhancing efficacies of agrochemicals, especially rain resistance, and the viewpoint of excellent formulation stability of agrochemical compositions, preferably 0.5/1 or more, and more preferably 0.8/1 or more; and preferably 2/1 or less, and more preferably 1.2/1 or less.

From the handleability, the efficacy-enhancing agent composition for amino acid-based agrochemicals of the present invention preferably contains water. Further, it is preferably a liquid composition. Furthermore, it is preferably a liquid composition containing water.

As the water, tap water, distilled water, ion-exchanged water or the like may be used within such a range that does not impair the effects of the efficacy-enhancing agent composition for amino acid-based agrochemicals of the present invention; and ion-exchange water is preferred from the viewpoint of the stability.

From the viewpoint of the handleability, the content of water in the efficacy-enhancing agent composition for amino acid-based agrochemicals of the present invention is preferably 5% by mass or more, more preferably 15% by mass or more, further preferably 25% by mass or more, and further more preferably 28% by mass or more; and from the viewpoint of the economic efficiency such as transport costs, it is preferably 50% by mass or less, more preferably 40% by mass or less, and further preferably 35% by mass or less.

The efficacy-enhancing agent composition for amino acid-based agrochemicals of the present invention may optionally contain compounds other than these components, for example, compounds used as oil or surfactants.

The efficacy-enhancing agent composition for amino acid-based agrochemicals of the present invention is produced by mixing, for example, the compound (A), if necessary, the compound (B), the compound (C) and water, and stirring the resultant mixture. Further, mixing of these components may be carried out either by adding these components together or adding each component separately. When they are added separately, they may be added in whatever order.

<Agrochemical Composition>

An agrochemical composition of the present invention contains the efficacy-enhancing agent composition for amino acid-based agrochemicals of the present invention, an amino acid-based agrochemical active ingredient (D), and water.

Further, an agrochemical composition containing the compound (A), the amino acid-based agrochemical active ingredient (D), and water is also an agrochemical composition of the present invention.

Further, an agrochemical composition containing the compound (A), the compound (B), the amino acid-based agrochemical active ingredient (D), and water is also an agrochemical composition of the present invention.

Further, an agrochemical composition containing the compound (A), the compound (C), the amino acid-based agrochemical active ingredient (D), and water is also an agrochemical composition of the present invention.

Further, an agrochemical composition containing the compound (A), the compound (B), the compound (C), the amino acid-based agrochemical active ingredient (D), and water is also an agrochemical composition of the present invention.

As the amino acid-based agrochemical active ingredient (D), agrochemical active ingredients (active component) of amino acid-based herbicides are exemplified. As the agrochemical active ingredients (active component) of amino acid-based herbicides, exemplified is at least one compound selected from glyphosate (N-(phosphonomethyl)glycine or salts thereof), bialaphos (sodium salt of L-2-amino-4-[(hydroxy)(methyl)=phosphinoyl]butyryl-L-alanyl-L-alanine) and glufosinate (ammonium DL-homoalanine-4-yl(methyl) phosphinate). From the viewpoint of enhancing efficacies of agrochemicals, especially rain resistance, and the viewpoint of excellent formulation stability of agrochemical compositions, preferred is at least one compound selected from glyphosate (N-(phosphonomethyl)glycine or salts thereof) and glufosinate (ammonium DL-homoalanine-4-yl(methyl) phosphinate); and more preferred is glyphosate (N-(phosphonomethyl)glycine or salts thereof). These may be agriculturally acceptable salts. For blending with an agrochemical composition, these may be used in the form of an aqueous solution, a liquid, a wettable powder or the like, which contains them.

The agrochemical composition of the present invention contains the amino acid-based agrochemical active ingredient (D) in an amount of, from the viewpoint of the economic efficiency such as transport costs, preferably 10% by mass or more, more preferably 20% by mass or more, further preferably 30% by mass or more and further more preferably 35% by mass or more; and from the viewpoint of excellent formulation stability of agrochemical compositions, preferably 70% by mass or less, more preferably 60% by mass or less, further preferably 50% by mass or less and further more preferably 45% by mass or less.

In the agrochemical composition of the present invention, preferred structures of or the mass ratios of the contents of the compounds (A1), (A2), (A3), (A4), (B) and (C) may be selected from the matters mentioned on the efficacy-enhancing agent composition for amino acid-based agrochemicals of the present invention.

The agrochemical composition of the present invention contains the compound (A1) in an amount of: preferably 2% by mass or more, more preferably 3% by mass or more, further preferably 3.4% by mass or more, further more preferably 3.6% by mass or more, and further more preferably 3.8% by mass or more from the viewpoint of enhancing efficacies of agrochemicals, especially rain resistance, and the viewpoint of excellent formulation stability of agrochemical compositions; and, preferably 10% by mass or less, more preferably 8% by mass or less, further preferably 6% by mass or less, further more preferably 5.2% by mass or less, and further more preferably 4.5% by mass or less from the viewpoint of the economic efficiency.

The agrochemical composition of the present invention contains the compound (A2) within such a range that does not impair the effects of the present invention. The agrochemical composition of the present invention contains the compound (A2) in an amount of: preferably 0.5% by mass or more, more preferably 1.0% by mass or more, further preferably 1.2% by mass or more and further more preferably 1.5% by mass or more from the viewpoint of balancing the effects and the economic efficiency; and preferably 5.0% by mass or less, more preferably 3.0% by mass or less, further preferably 2.8% by mass or less, further more preferably 2.6% by mass or less, and further more preferably 2.0% by mass or less from the viewpoint of not deteriorating the effects of the present invention.

The agrochemical composition of the present invention contains the compound (A3) within such a range that does not impair the effects of the present invention. The agrochemical composition of the present invention contains the compound (A3) in an amount of: preferably 0.05% by mass or more, more preferably 0.1% by mass or more and further preferably 0.2% by mass or more from the viewpoint of balancing the effects and the economic efficiency; and preferably 2.0% by mass or less, more preferably 1.0% by mass or less, further preferably 0.8% by mass or less, further more preferably 0.6% by mass or less, and further more preferably 0.3% by mass or less from the viewpoint of not deteriorating the effects of the present invention.

The agrochemical composition of the present invention may contain the compound (A4) within such a range that does not impair the effects of the present invention. The agrochemical composition of the present invention contains the compound (A4) in an amount of: preferably 0.5% by mass or more, more preferably 1.0% by mass or more, further preferably 1.2% by mass or more, further more preferably 1.5% by mass or more, and further more preferably 1.8% by mass or more from the viewpoint of balancing the effects and the economic efficiency; and preferably 5.0% by mass or less, more preferably 3.0% by mass or less, further preferably 2.4% by mass or less, and further more preferably 2.0% by mass or less from the viewpoint of not deteriorating the effects of the present invention.

In the agrochemical composition of the present invention, from the viewpoint of enhancing efficacies of agrochemicals, especially rain resistance, and the viewpoint of excellent formulation stability of agrochemical compositions, the mass ratio of the compound (A1) to the amino acid-based agrochemical active ingredient (D), [content of compound (A1)]/[content of amino acid-based agrochemical active ingredient (D)], is preferably 1/35 or more, more preferably 1/20 or more, further preferably 1/15 or more, and further more preferably 1/12 or more; and preferably 1/1 or less, more preferably 2/5 or less, further preferably 1/5 or less, and further more preferably 1/7 or less.

The agrochemical composition of the present invention contains the compound (B) in an amount of: from the viewpoint of enhancing efficacies of agrochemicals, especially rain resistance, preferably 0.1% by mass or more, more preferably 0.3% by mass or more, further preferably 0.5% by mass or more, further more preferably 0.7% by mass or more, further more preferably 0.8% by mass or more, further more preferably 1.0% by mass or more, and further more preferably 1.2% by mass or more; and from the viewpoint of the economic efficiency, preferably 5.0% by mass or less, more preferably 3.0% by mass or less, further preferably 2.0% by mass or less, further more preferably 1.8% by mass or less, and further more preferably 1.5% by mass or less.

The agrochemical composition of the present invention contains the compound (C) in an amount of: from the viewpoint of enhancing efficacies of agrochemicals, especially rain resistance, preferably 0.1% by mass or more, more preferably 0.3% by mass or more, further preferably 0.5% by mass or more, further more preferably 0.7% by mass or more, further more preferably 0.8% by mass or more, further more preferably 1.0% by mass or more, and further more preferably 1.2% by mass or more; and from the viewpoint of the economic efficiency, preferably 5.0% by mass or less, more preferably 3.0% by mass or less, further preferably 2.0% by mass or less, further more preferably 1.8% by mass or less, and further more preferably 1.5% by mass or less.

The agrochemical composition of the present invention contains water from the handleability; and is preferably in the form of a liquid composition containing water. The agrochemical composition of the present invention contains water in an amount of: from the viewpoint of the handleability, preferably 20% by mass or more, more preferably 30% by mass or more, further preferably 40% by mass or more, and further more preferably 45% by mass or more; and from the viewpoint of the economic efficiency such as transport costs, preferably 70% by mass or less, more preferably 60% by mass or less, and further preferably 55% by mass or less.

The efficacy-enhancing agent composition for amino acid-based agrochemicals of the present invention may optionally contain compounds other than the compounds (A), (B) and (C), the agrochemical active ingredient (D) and water, for example, a solvent (propylene glycol monomethyl ether, etc.), a chelating agent, a pH adjusting agent, an inorganic salt and a thickener.

According to the present invention, there is provided a method for producing an agrochemical composition, which includes mixing the efficacy-enhancing agent composition for amino acid-based agrochemicals of the present invention, the amino acid-based agrochemical active ingredient (D) and water with one another. In this production method, the matters mentioned on the efficacy-enhancing agent composition for amino acid-based agrochemicals and the agrochemical composition of the present invention are appropriately applicable. For example, the content of each component in the agrochemical composition can be replaced with and used as a formulation amount as a ratio in raw materials to be blended.

<Weeding Method>

A weeding method of the present invention is to spray on a plant an agrochemical spray solution prepared from the agrochemical composition of the present application. In the weeding method of the present invention, a concentration of the compound (A1) in the agrochemical spray solution may be selected from 30 ppm or more, 100 ppm or more, 120 ppm or more, 150 ppm or more, 170 ppm or more, or 200 ppm or more, from the viewpoint of enhancing efficacies of agrochemicals, especially rain resistance; and it may be selected from 50,000 ppm or less, 5,000 ppm or less, 2,000 ppm or less, 1,000 ppm or less, 600 ppm or less, 500 ppm or less, or 400 ppm or less, from the viewpoint of the economic efficiency. Further, in the weeding method of the present invention, the agrochemical spray solution is sprayed in an ratio of preferably 50 L/ha or more, more preferably 200 L/ha or more, further preferably 400 L/ha or more, and further more preferably 500 L/ha or more; and preferably 1,000 L/ha or less, more preferably 800 L/ha or less, and more preferably 600 L/ha or less.

The weeding method of the present invention is to apply a predetermined spray solution to a weed, which is a target plant to be eliminated. In the agricultural field, weeds grow in crop lands or around there, and are recognized as herbs that cause damages to crop production. Further, in the fields other than agriculture, they naturally grow in lands, not limited to crop lands, that is non-crop lands such as roads, tracklaying sites, embankments, plant sites, housing sites, lawn sites and gardens, and they are recognized as herbs that disturb the function of a land or cause problems in terms of the protection against disasters or the landscape. In the present invention, all of these herbs are regarded as weeds. Weeds include broad leaf weeds, gramineous weeds and others. Broad leaf weeds have reticulate veins, different from weeds like gramineous weeds having linear leaves or weeds having parallel veins.

As weeds, which would be a target of the weeding method of the present invention, exemplified are broad leaf weeds. Examples of broad leaf weeds include a morning glory (*Ipomoea nil*), a velvet leaf (*Abutilon theophrasti*), a Japanese bindweed (*Calystegia japonica*), a white clover (*Trifolium repens*), a dandelion (*Taraxacum*), a sorrel vine (*Cayratia japonica*), a tall goldenrod (*Solidago altissima*), a hairy fleabane (*Conyza bonariensis*), a large-leaved beggarticks (*Bidens frondosa*), Iodori, *Rorippa indica*, *Persicaria longiseta*, *Amaranthus lividus* var. *ascendens*, a Persian speedwell (*Veronica persica*), an Asiatic plantain (*Plantago asiatica*), a cocklebur (*Xanthium strumarium*), a ground ivy (*Glechoma hederacea* ssp. *grandis*), a yellow sorrel (*Oxalis corniculata*), a Japanese hop (*Humulus japonicus*), a galingale (*Cyperus microiria*), a narrow-leaved vetch (*Vicia angustifolia*), *Rumex japonicus, Euphorbia pseudochamaesyce, Lactuca stolonifera*, a white goosefoot (*Chenopodium album* var. *album.*), *Rorippa islandica*, a hose tail (*Equisetum arvense*), a purslane (*Portulaca oleracea*), a dandelion (*Taraxacum officinale*), a plume poppy (*Macleaya cordata*), a dayflower (*Commelina communis*), a dokudami (*Houttuynia cordata*), a shepherd's purse (*Capsella bursa-pastoris*), a common sow thistle (*Sonchus oleraceus*), a groundsel (*Senecio vulgaris*), *Stellaria alsine* var. *undulata*, a chickweed (*Stellaria media*), a cudweed (*Gnaphalium multiceps*), a coco grass (*Cyperus rotundus*), a Philadelphia fleabane (*Erigeron philadelphicus*), a sweet scabious (*Erigeron annuus*), a horse-weed (*Erigeron canadensis*), a ragweed (*Ambrosia artemisiifolia* var. *elatior*), a henbit (*Lamium amplexicaule*), a bedstraw (*Galium spurium* var. *echinospermon*), a Japanese mugwort (*Artemisia prpinceps*), and a horse nettle (*Solanum carolinense*); and from the viewpoint of enhancing efficacies of agrochemicals, especially rain resistance, a morning glory and a velvet leaf are preferred.

As weeds, which would be a target of the weeding method of the present invention, exemplified are gramineous weeds. Examples of gramineous weeds include a barnyard grass (*Echinochloa curs-galli*), a green foxtail (*Setaria viridis*), a yellow foxtail (*Setaria lutescens*), *Setaria viridis purpurascens*, an annual bluegrass (*Poa annua*), a short-awn foxtail (*Alopecurus aequalis*), a love grass (*Eragrostis multicaulis*), *Digitaria violascens*, a finger grass (*Digitaria sanguinalis*), a bay grass (*Eragrostis ferruginea*), an orchard grass (*Dactylis glomerata*), an eulalia (*Miscanthus sinensis*), *Paspalum thunbergii*, a cogon grass (*Imperata cylindrica* var. *koenigii*), *Pennisetum alopecurioides*, a reed (*Phragmites communis*), and bamboo grasses (*Sasa*); and from the viewpoint of enhancing efficacies of agrochemicals, especially rain resistance, a barnyard grass is preferred.

The weeding method of the present invention may be intended for weeds selected from broad leaf weeds and gramineous weeds. Further, the weeding method of the present invention may be intended for weeds selected from a barnyard grass, a morning glory, and a velvet leaf. Further, the weeding method of the present invention may be intended for a barnyard grass.

Hereinafter, examples of the present invention are indicated. The matters mentioned on the efficacy-enhancing agent composition for amino acid-based agrochemicals, the agrochemical composition and the weeding method according to the present invention can be appropriately applied to these examples.

<1>

An efficacy-enhancing agent composition for amino acid-based agrochemicals, containing a compound (A1) represented by the following general formula (1-1), optionally a compound (A2) represented by the following general formula (1-2), and optionally a compound (A3) represented by the following general formula (1-3), wherein:

the mass ratio of the content of the compound (A3) to the sum of the contents of the compound (A1) and the compound (A2), [content of compound (A3)]/[sum of contents of compounds (A1) and (A2)], is 0/100 or more and 10/90 or less; and the mass ratio of the content of the compound (A2) to the content of the compound (A1), [content of compound (A2)]/[content of compound (A1)], is 0/100 or more and 50/50 or less.

[Chemical Formula 7]

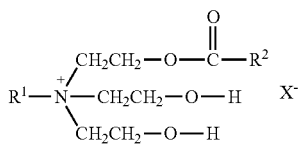 (1-1)

[Chemical Formula 8]

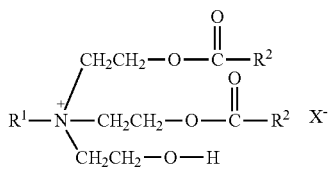 (1-2)

[Chemical Formula 9]

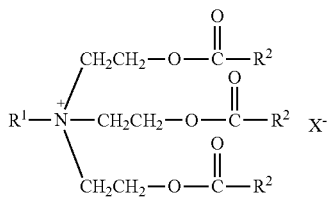 (1-3)

[In the formulas, $R^1$ denotes a linear alkyl group having 1 or more and 4 or less carbon atoms, a linear alkenyl group having 2 or more and 4 or less carbon atoms, a branched alkyl group having 3 or more and 4 or less carbon atoms, or a branched alkenyl group having 3 or more and 4 or less carbon atoms, preferably a linear alkyl group having 1 or more and 4 or less carbon atoms, more preferably a linear alkyl group having 1 or more or 2 or less carbon atoms, and more preferably a linear alkyl group having 1 carbon atom;

$R^2$ denotes a linear or branched alkyl or alkenyl group having 5 or more and 11 or less carbon atoms, preferably a linear or branched alkyl or alkenyl group having 7 or more and 11 or less carbon atoms, more preferably a linear or branched alkyl group having 7 or more and 11 or less carbon atoms, further more preferably a linear alkyl group having 7 or more and 11 or less carbon atoms, further more preferably a linear alkyl group having 7 or more and 9 or less carbon atoms, and further more preferably a linear alkyl group having 9 carbon atoms; and $X^-$ denotes a counter ion, preferably a halogenide ion or an alkyl sulfate anion, further preferably an alkyl sulfate anion, further more preferably a methyl sulfate anion or an ethyl sulfate anion, and further more preferably a methyl sulfate anion.]

<2>

An efficacy-enhancing agent composition for amino acid-based agrochemicals, containing a compound (A1) represented by the following general formula (1-1), optionally a compound (A2) represented by the following general formula (1-2), optionally a compound (A3) represented by the following general formula (1-3), and optionally a compound (A4) represented by the following general formula (1-4), wherein:

the mass ratio of the content of the compound (A3) to the sum of the contents of the compound (A1) and the compound (A2), [content of compound (A3)]/[sum of contents of compounds (A1) and (A2)], is 0/100 or more and 10/90 or less;

the mass ratio of the content of the compound (A2) to the content of the compound (A1), [content of compound (A2)]/[content of compound (A1)], is 0/100 or more and 50/50 or less; and the mass ratio of the content of the compound (A4) to the sum of the contents of the compound (A1) and the compound (A2), [content of compound (A4)]/[sum of contents of compounds (A1) and (A2)], is 0/100 or more and 50/50 or less.

[Chemical Formula 10]

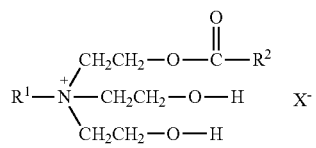 (1-1)

[Chemical Formula 11]

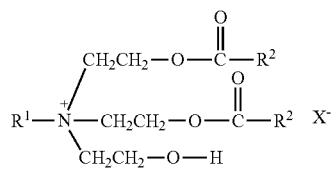 (1-2)

[Chemical Formula 12]

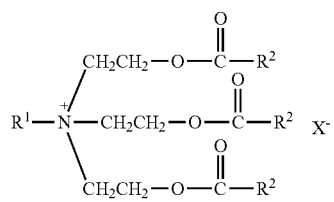 (1-3)

[Chemical Formula 13]

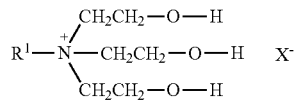 (1-4)

[In the formulas, $R^1$ denotes a linear alkyl group having 1 or more and 4 or less carbon atoms, a linear alkenyl group having 2 or more and 4 or less carbon atoms, a branched alkyl group having 3 or more and 4 or less carbon atoms, or a branched alkenyl group having 3 or more and 4 or less carbon atoms, preferably a linear alkyl group having 1 or more and 4 or less carbon atoms, more preferably a linear alkyl group having 1 or more or 2 or less carbon atoms, and more preferably a linear alkyl group having 1 carbon atom;

$R^2$ denotes a linear or branched alkyl or alkenyl group having 5 or more and 11 or less carbon atoms, preferably a linear or branched alkyl or alkenyl group having 7 or more and 11 or less carbon atoms, more preferably a linear or branched alkyl group having 7 or more and 11 or less carbon atoms, further more preferably a linear alkyl group having 7 or more and 11 or less carbon atoms, further more preferably a linear alkyl group having 7 or more and 9 or less carbon atoms, and further more preferably a linear alkyl group having 9 carbon atoms; and $X^-$ denotes a counter ion, preferably a halogenide ion or an alkyl sulfate anion, further preferably an alkyl sulfate anion, further more preferably a methyl sulfate anion or an ethyl sulfate anion, and further more preferably a methyl sulfate anion.]

<3>

An efficacy-enhancing agent composition for amino acid-based agrochemicals, containing a compound (A1) represented by the following general formula (1-1), a compound (A2) represented by the following general formula (1-2), a compound (A3) represented by the following general formula (1-3), and a compound (A4) represented by the following general formula (1-4), wherein:

the mass ratio of the content of the compound (A3) to the sum of the contents of the compound (A1) and the compound (A2), [content of compound (A3)]/[sum of contents of compounds (A1) and (A2)], is 1/99 or more and 10/90 or less;

the mass ratio of the content of the compound (A2) to the content of the compound (A1), [content of compound (A2)]/[content of compound (A1)], is 5/95 or more and 50/50 or less; and the mass ratio of the content of the compound (A4) to the sum of the contents of the compound (A1) and the compound (A2), [content of compound (A4)]/[sum of contents of compounds (A1) and (A2)], is 10/90 or more and 50/50 or less.

[Chemical Formula 14]

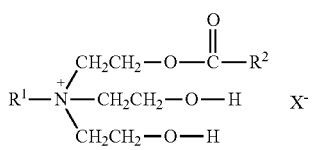

(1-1)

[Chemical Formula 15]

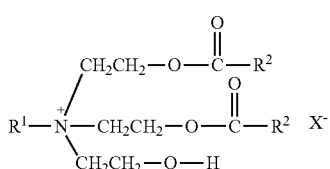

(1-2)

[Chemical Formula 16]

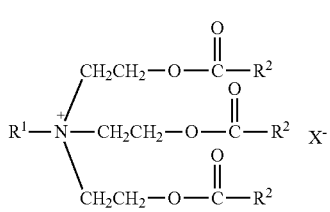

(1-3)

-continued

[Chemical Formula 17]

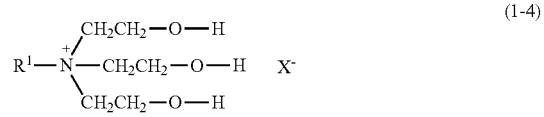

(1-4)

[In the formulas, $R^1$ denotes a linear alkyl group having 1 or more and 4 or less carbon atoms, a linear alkenyl group having 2 or more and 4 or less carbon atoms, a branched alkyl group having 3 or more and 4 or less carbon atoms, or a branched alkenyl group having 3 or more and 4 or less carbon atoms, preferably a linear alkyl group having 1 or more and 4 or less carbon atoms, more preferably a linear alkyl group having 1 or more or 2 or less carbon atoms, and more preferably a linear alkyl group having 1 carbon atom;

$R^2$ denotes a linear or branched alkyl or alkenyl group having 5 or more and 11 or less carbon atoms, preferably a linear or branched alkyl or alkenyl group having 7 or more and 11 or less carbon atoms, more preferably a linear or branched alkyl group having 7 or more and 11 or less carbon atoms, further more preferably a linear alkyl group having 7 or more and 11 or less carbon atoms, further more preferably a linear alkyl group having 7 or more and 9 or less carbon atoms, and further more preferably a linear alkyl group having 9 carbon atoms; and $X^-$ denotes a counter ion, preferably a halogenide ion or an alkyl sulfate anion, further preferably an alkyl sulfate anion, further more preferably a methyl sulfate anion or an ethyl sulfate anion, and further more preferably a methyl sulfate anion.]

<4>

The efficacy-enhancing agent composition for amino acid-based agrochemicals described in any one of the above <1> to <3>, wherein the compound (A1) is a compound of the general formula (1-1) in which $R^1$ is a linear alkyl group with 1 or more and 3 or less carbon atoms, preferably a linear alkyl group with 1 or more and 2 or less carbon atoms, and more preferably a linear alkyl group with 1 carbon atom.

<5>

The efficacy-enhancing agent composition for amino acid-based agrochemicals described in any one of the above <1> to <4>, wherein the compound (A1) is a compound of the general formula (1-1) in which $R^2$ is a linear alkyl group with 7 or more and 11 or less carbon atoms, preferably a linear alkyl group with 7 or more and 9 or less carbon atoms, and more preferably a linear alkyl group with 9 carbon atoms.

<6>

The efficacy-enhancing agent composition for amino acid-based agrochemicals described in any one of the above <1> to <5>, wherein the compound (A1) is a compound of the general formula (1-1) in which $X^-$ is a halogenide ion or an alkyl sulfate anion, preferably an alkyl sulfate anion, more preferably a methyl sulfate anion or an ethyl sulfate anion, further more preferably a methyl sulfate anion.

<7>

The efficacy-enhancing agent composition for amino acid-based agrochemicals described in any one of the above <1> to <6>, wherein the composition contains the compound (A1) in an amount of 25% by mass or more, preferably 27% by mass or more, more preferably 30% by mass or more, and further preferably 33% by mass or more; and 60% by mass or less, preferably 50% by mass or less, and more preferably 40% by mass or less.

<8>

The efficacy-enhancing agent composition for amino acid-based agrochemicals described in any one of the above <1> to <7>, wherein the mass ratio of the content of the compound (A3) to the sum of the contents of the compound (A1) and the compound (A2), [content of compound (A3)]/[sum of contents of compounds (A1) and (A2)], is 1/99 or more, preferably 2/98 or more, more preferably 3/97 or more, and further preferably 4/96 or more; and 9/91 or less, preferably 7/93 or less, more preferably 6/94 or less, and further preferably 5/95 or less.

<9>

The efficacy-enhancing agent composition for amino acid-based agrochemicals described in any one of the above <1> to <8>, wherein the mass ratio of the content of the compound (A2) to the content of the compound (A1), [content of compound (A2)]/[content of compound (A1)], is 5/95 or more, preferably 15/85 or more, more preferably 20/80 or more, more preferably 25/75 or more, further preferably 28/72 or more; and 46/54 or less, preferably 44/54 or less, more preferably 40/60 or less, further preferably 37/63 or less, and further more preferably 30/70 or less.

<10>

The efficacy-enhancing agent composition for amino acid-based agrochemicals described in any one of the above <2> to <9>, wherein the composition contains at least one compound selected from the compound (A2) represented by the general formula (1-2), the compound (A3) represented by the general formula (1-3) and the compound (A4) represented by the general formula (1-4).

<11>

The efficacy-enhancing agent composition for amino acid-based agrochemicals described in any one of the above <1> to <10>, wherein the composition contains the compound (A2) in an amount of 1% by mass or more, preferably 5% by mass or more, and preferably 10% by mass or more; and 25% by mass or less, preferably 23% by mass or less, more preferably 19% by mass or less, and further preferably 15% by mass or less.

<12>

The efficacy-enhancing agent composition for amino acid-based agrochemicals described in any one of the above <1> to <11>, wherein the composition contains the compound (A3) in an amount of 0.5% by mass or more, preferably 1.0% by mass or more, and more preferably 1.3% by mass or more; and 6% by mass or less, preferably 5.3% by mass or less, more preferably 4% by mass or less, further preferably 3.3% by mass or less, further more preferably 2.2% by mass or less, and further more preferably 2.0% by mass or less.

<13>

The efficacy-enhancing agent composition for amino acid-based agrochemicals described in any one of the above <2> to <12>, wherein the composition contains the compound (A4) and the compound (A4) is present in an amount of 1% by mass or more, preferably 5% by mass or more, more preferably 10% by mass or more, and further preferably 15% by mass or more; and 25% by mass or less, preferably 20% by mass or less, and more preferably 18% by mass or less.

<14>

The efficacy-enhancing agent composition for amino acid-based agrochemicals described in any one of the above <1> to <13>, wherein the mass ratio of the content of the compound (A4) to the sum of the contents of the compound (A1) and the compound (A2), [content of compound (A4)]/[sum of contents of compounds (A1) and (A2)], is 10/90 or more, preferably 12/88 or more, more preferably 15/85 or more, further preferably 20/80 or more, and further more preferably 24/76 or more; and 40/60 or less, preferably 35/65 or less, and more preferably 30/70 or less.

<15>

The efficacy-enhancing agent composition for amino acid-based agrochemicals described in any one of the above <2> to <14>, wherein the ratio of the compound (A1) in the total of the contents of the compounds (A1), (A2), (A3) and (A4) is 40% by mass or more, preferably 42% by mass or more, more preferably 45% by mass or more, further preferably 48% by mass or more, and further more preferably 50% by mass or more; and 100% by mass or less, preferably 80% by mass or less, more preferably 70% by mass or less, and further preferably 60% by mass or less.

<16>

The efficacy-enhancing agent composition for amino acid-based agrochemicals described in any one of the above <1> to <15>, further containing at least one compound (B) selected from compounds represented by the following general formula (B1).

$$R^{1b}O-(EO)_l-R^{2b} \quad (B1)$$

[In the general formula (B1), $R^{1b}$ denotes a linear or branched alkyl or alkenyl group with 10 or more and 16 or less carbon atoms;

EO denotes an ethyleneoxy group;

l denotes an average addition molar number of ethyleneoxy group and is a number of 3 or more and 40 or less; and $R^{2b}$ denotes a hydrogen atom or a methyl group.]

<17>

The efficacy-enhancing agent composition for amino acid-based agrochemicals described in the above <16>, wherein the compound (B) is a compound in which $R^{1b}$ of the general formula (B1) is a linear or branched alkyl or alkenyl group with 10 or more and 14 or less carbon atoms, preferably a linear or branched alkyl or alkenyl group with 10 or more and 12 or less carbon atoms, more preferably a linear or branched alkyl or alkenyl group with 12 carbon atoms, and further preferably a linear alkyl group with 12 carbon atoms.

<18>

The efficacy-enhancing agent composition for amino acid-based agrochemicals described in the above <16> or <17>, wherein the compound (B) is a compound in which l of the general formula (B1) is 4 or more, preferably 5 or more, and more preferably 6 or more; and 30 or less, preferably 20 or less, more preferably 10 or less, and further preferably 8 or less.

<19>

The efficacy-enhancing agent composition for amino acid-based agrochemicals described in any one of the above <16> to <18>, wherein the compound (B) is a compound in which $R^{2b}$ of the general formula (B1) is a hydrogen atom.

<20>

The efficacy-enhancing agent composition for amino acid-based agrochemicals described in any one of the above <16> to <19>, wherein the composition contains the compound (B) in an amount of 2% by mass or more, preferably 4% by mass or more, more preferably 5% by mass or more, further preferably 8% by mass or more, and further more preferably 10% by mass or more; and 20% by mass or less, preferably 15% by mass or less, and more preferably 12% by mass or less.

<21>

The efficacy-enhancing agent composition for amino acid-based agrochemicals described in any one of the above <1> to <20>, further containing at least one compound (C) selected from a compound (C1) represented by the following general formula (C1) and a compound (C2) represented by the following general formula (C2).

$$R^{1c}-O-[(PO)_m/(EO)_n]-R^{2c} \quad (C1)$$

[In the general formula (C1)
$R^{1c}$ denotes a linear or branched alkyl or alkenyl group with 6 or more and 12 or less carbon atoms;
PO denotes a propyleneoxy group;
EO denotes an ethyleneoxy group;
m denotes an average addition molar number of propyleneoxy group and is a number of 1 or more and 25 or less;
n denotes an average addition molar number of ethyleneoxy group and is a number of 0 or more and 4 or less; and
$R^{2c}$ denotes a hydrogen atom or a methyl group.
The sign "/" means that PO and EO are bonded in a random form or a block form.]

$$R^{3c}-OH \quad (C2)$$

[In the general formula (C2),
$R^{3c}$ denotes a linear or branched alkyl group with 8 or more and 14 or less carbon atoms.]

<22>

The efficacy-enhancing agent composition for amino acid-based agrochemicals described in the above <21>, wherein the compound (C) is the compound (C1) of the general formula (C1) in which $R^{1c}$ is a linear or branched alkyl or alkenyl group with 8 or more and 12 or less carbon atoms, preferably a linear or branched alkyl or alkenyl group with 8 or more and 10 or less carbon atoms, more preferably a linear alkyl group with 8 or more and 10 or less carbon atoms, and further preferably a linear alkyl group with 8 carbon atoms.

<23>

The efficacy-enhancing agent composition for amino acid-based agrochemicals described in the above <21> or <22>, wherein the compound (C) is the compound (C1) of the general formula (C1) in which m is 2 or more, and preferably 3 or more; and 10 or less, preferably 5 or less, more preferably 4 or less and further preferably 3 or less.

<24>

The efficacy-enhancing agent composition for amino acid-based agrochemicals described in any one of the above <21> to <23>, wherein the compound (C) is the compound (C1) of the general formula (C1) in which n is 3 or less, preferably 2 or less, more preferably 1 or less and further preferably 0.

<25>

The efficacy-enhancing agent composition for amino acid-based agrochemicals described in any one of the above <21> to <24>, wherein the compound (C) is the compound (C1) in which the ratio of m to the total of m and n, m/(m+n), is 0.5 or more, preferably 0.6 or more, more preferably 0.7 or more, further preferably 0.8 or more, and further more preferably 0.9 or more; and 1.0 or less.

<26>

The efficacy-enhancing agent composition for amino acid-based agrochemicals described in any one of the above <21> to <25>, wherein the compound (C) is a compound of the general formula (C1) in which $R^{2c}$ is a hydrogen atom.

<27>

The efficacy-enhancing agent composition for amino acid-based agrochemicals described in any one of the above <21> to <26>, wherein the compound (C) is the compound (C2) of the general formula (C2) in which $R^{3c}$ is a linear or branched alkyl group with 8 or more and 12 or less carbon atoms, preferably a linear or branched alkyl group with 8 or more and 10 or less carbon atoms, more preferably a linear alkyl group with 8 or more and 10 or less carbon atoms, and further preferably a linear alkyl group with 10 carbon atoms.

<28>

The efficacy-enhancing agent composition for amino acid-based agrochemicals described in any one of the above <21> to <27>, wherein the composition contains, as the compound (C), at least one compound selected from the compounds (C1)

<29>

The efficacy-enhancing agent composition for amino acid-based agrochemicals described in any one of the above <21> to <28>, wherein the composition contains the compound (C) in an amount of 2% by mass or more, preferably 4% by mass or more, more preferably 5% by mass or more, further preferably 8% by mass or more, and further more preferably 10% by mass or more; and 20% by mass or less, more preferably 15% by mass or less, and further preferably 12% by mass or less.

<30>

The efficacy-enhancing agent composition for amino acid-based agrochemicals described in any one of the above <16> to <29>, wherein the composition contains the compound (B) and the mass ratio of the content of the compound (A1) to the content of the compound (B), [content of compound (A1)]/[content of compound (B)], is 1.5/1 or more, preferably 2/1 or more, and more preferably 2.5/1 or more; and 10/1 or less, preferably 7/1 or less, more preferably 5.5/1 or less, further preferably 4/1 or less, and further more preferably 3/1 or less.

<31>

The efficacy-enhancing agent composition for amino acid-based agrochemicals described in any one of the above <21> to <30>, wherein the composition contains the compound (C) and the mass ratio of the content of the compound (A1) to the content of the compound (C), [content of compound (A1)]/[content of compound (C)], is 1.5/1 or more, preferably 2/1 or more, and more preferably 2.5/1; and 10/1 or less, preferably 7/1 or less, more preferably 5.5/1 or less, further preferably 4/1 or less, and further more preferably 3/1 or less.

<32>

The efficacy-enhancing agent composition for amino acid-based agrochemicals described in any one of the above <21> to <31>, wherein the composition contains the compounds (B) and (C) and the mass ratio of the content of the compound (A1) to the sum of the contents of the compounds (B) and (C), [content of compound (A1)]/[sum of contents of compounds (B) and (C)], is 1.5/1 or more, preferably 2/1 or more, and more preferably 2.5/1 or more; and 7/1 or less, preferably 5.5/1 or less, more preferably 4/1 or less, and further preferably 3/1 or less.

<33>

The efficacy-enhancing agent composition for amino acid-based agrochemicals described in any one of the above <21> to <32>, wherein the composition contains the compounds (B) and (C) and the mass ratio of the content of the compound (B) to the content of the compound (C), [content of compound (B)]/[content of compound (C)], is 0.5/1 or more, and preferably 0.8/1; and 2/1 or less, and preferably 1.2/1 or less.

<34>
The efficacy-enhancing agent composition for amino acid-based agrochemicals described in any one of the above <1> to <33>, wherein the composition is a liquid composition containing water.
<35>
The efficacy-enhancing agent composition for amino acid-based agrochemicals described in the above <34>, wherein the content of the water is 5% by mass or more, preferably 15% by mass or more, more preferably 25% by mass or more, and further preferably 28% by mass or more; and 50% by mass or less, preferably 40% by mass or less, and more preferably 35% by mass or less.
<36>
An agrochemical composition containing an efficacy-enhancing agent composition for amino acid-based agrochemicals described in any one of the above <1> to <35>, an amino acid-based agrochemical active ingredient (D), and water.
<37>
The agrochemical composition described in the above <36>, wherein the amino acid-based agrochemical active ingredient (D) is glyphosate or glufosinate, preferably glyphosate; or N-(phosphonomethyl)glycine or salts thereof, or ammonium DL-homoalanine-4-yl(methyl)phosphinate, preferably N-(phosphonomethyl)glycine or salts thereof.
<38>
The agrochemical composition described in the above <36> or <37>, wherein the amino acid-based agrochemical active ingredient (D) is at least one compound selected from N-(phosphonomethyl)glycine or salts thereof, sodium salt of L-2-amino-4-[(hydroxy)(methyl)=phosphinoyl]butyryl-L-alanyl-L-alanine and ammonium DL-homoalanine-4-yl(methyl)phosphinate; preferably at least one compound selected from N-(phosphonomethyl)glycine or salts thereof and ammonium DL-homoalanine-4-yl(methyl)phosphinate; and more preferably N-(phosphonomethyl)glycine or salts thereof.
<39>
The agrochemical composition described in any one of the above <36> to <38>, wherein the composition contains the amino acid-based agrochemical active ingredient (D) in an amount of 10% by mass or more, preferably 20% by mass or more, more preferably 30% by mass or more, and further preferably 35% by mass or more; and 70% by mass or less, preferably 60% by mass or less, more preferably 50% by mass or less, and further preferably 45% by mass or less.
<40>
The agrochemical composition described in any one of the above <36> to <38>, wherein the composition contains the compound (A1) in an amount of 2% by mass or more, preferably 3% by mass or more, more preferably 3.4% by mass or more, further preferably 3.6% by mass or more, and further more preferably 3.8% by mass or more; and 10% by mass or less, preferably 8% by mass or less, more preferably 6% by mass or less, further preferably 5.2% by mass or less, and further more preferably 4.5% by mass or less.
<41>
The agrochemical composition described in any one of the above <36> to <40>, wherein the composition contains the compound (A2) in an amount of 0.5% by mass or more, preferably 1.0% by mass or more, more preferably 1.2% by mass or more, further more preferably 1.5% by mass or more; and 5.0% by mass or less, preferably 3.0% by mass or less, more preferably 2.8% by mass or less, further preferably 2.6% by mass or less, and further more preferably 2.0% by mass or less.

<42>
The agrochemical composition described in any one of the above <36> to <41>, wherein the composition contains the compound (A3) in an amount of 0.05% by mass or more, preferably 0.1% by mass or more, and more preferably 0.2% by mass or more; and 2.0% by mass or less, preferably 1.0% by mass or less, more preferably 0.8% by mass or less, further preferably 0.6% by mass or less, and further more preferably 0.3% by mass or less.
<43>
The agrochemical composition described in any one of the above <36> to <42>, wherein the composition contains the compound (A4) and the compound (A4) is present in an amount of 0.5% by mass or more, preferably 1.0% by mass or more, more preferably 1.2% by mass or more, further more preferably 1.5% by mass or more, and further more preferably 1.8% by mass or more; and 5.0% by mass or less, preferably 3.0% by mass or less, more preferably 2.4% by mass or less, further preferably 2.0% by mass or less.
<44>
The agrochemical composition described in any one of the above <36> to <43>, wherein the composition contains the compound (B) and the compound (B) is present in an amount of 0.1% by mass or more, preferably 0.3% by mass or more, more preferably 0.5% by mass or more, further preferably 0.7% by mass or more, further more preferably 0.8% by mass or more, further more preferably 1.0% by mass or more, and further more preferably 1.2% by mass or more; and 5.0% by mass or less, preferably 3.0% by mass or less, more preferably 2.0% by mass or less, further preferably 1.8% by mass or less, and further more preferably 1.5% by mass or less.
<45>
The agrochemical composition described in any one of the above <36> to <44>, wherein the composition contains the compound (C) and the compound (C) is present in an amount of 0.1% by mass or more, preferably 0.3% by mass or more, more preferably 0.5% by mass or more, further preferably 0.7% by mass or more, further more preferably 0.8% by mass or more, further more preferably 1.0% by mass or more, and further more preferably 1.2% by mass or more; and 5.0% by mass or less, preferably 3.0% by mass or less, more preferably 2.0% by mass or less, further preferably 1.8% by mass or less, and further preferably 1.5% by mass or less.
<46>
The agrochemical composition described in any one of the above <36> to <45>, wherein the composition is a liquid composition containing water.
<47>
The agrochemical composition described in any one of the above <36> to <46>, wherein the composition contains water in an amount of 20% by mass or more, preferably 30% by mass or more, more preferably 40% by mass or more, and further preferably 45% by mass or more; and 70% by mass or less, preferably 60% by mass or less, and more preferably 55% by mass or less.
<48>
A method for weeding including spraying on a plant an agrochemical spray solution prepared from an agrochemical composition described in any one of the above <36> to <47>.
<49>
The method for weeding described in the above <48>, wherein the agrochemical spray solution has a concentration of the compound (A1) of 30 ppm or more, 100 ppm or more, 120 ppm or more, 150 ppm or more, 170 ppm or more, or 200 ppm or more; and 50,000 ppm or less, 5,000 ppm or less, 2,000 ppm or less, 1,000 ppm or less, 600 ppm or less, 500 ppm or less, or 400 ppm or less.
<50>
The method for weeding described in the above <48> or <49>, wherein the agrochemical spray solution is sprayed in a ratio of 50 L/ha or more, preferably 200 L/ha or more, more preferably 400 L/ha or more, and further preferably 500 L/ha; and 1,000 L/ha or less, preferably 800 L/ha or less, and more preferably 600 L/ha or less.
<51>
The method for weeding described in any one of the above <48> to <50>, wherein the plant is a weed selected from broad leaf weeds and gramineous weeds, preferably a weed selected from a barnyard grass, a morning glory and a velvet leaf, and more preferably a barnyard grass.
<52>
Use of the composition described in any one of the above <1> to <35> as an efficacy-enhancing agent for amino acid-based agrochemicals.
<53>
Use of the composition described in any one of the above <1> to <35> for enhancing an efficacy of an amino acid-based agrochemical.
<54>
A method of using the composition described in any one of the above <1> to <35> to enhance an efficacy of an amino acid-based agrochemical.
<55>
A method for producing an agrochemical composition, including mixing an efficacy-enhancing agent composition for amino acid-based agrochemicals described in any one of the above <1> to <35>, an amino acid-based agrochemical active ingredient (D), and water.

EXAMPLES

Implementation of the present invention will be described by referring to the Examples described below. The Examples are for illustrating the present invention, and not for liming the present invention.

Synthesis Example-1: Synthesis of Reaction Product a-1

Into a four-necked flask with a volume of 1 L, 254.6 g of capric acid and 371.2 g of triethanolamine (molar ratio of capric acid/triethanolamine=0.6/1) were fed, and reacted with each other for 1 hour under conditions at 140° C. and normal pressure, and then subjected to dehydration-condensation reaction for 2 hours at 180° C. under a reduced pressure of 220 hPa, so that ester amine was obtained. 199.9 g of the obtained ester amine and 100.1 g of dimethyl sulfate were used and reacted with each other for 2 hours at 60° C. for quaternization, so that Reaction Product a-1 was obtained. Reaction Product a-1 was a mixture containing the compounds (A1), (A2), (A3) and (A4) in a ratio indicated in Table 1. Further, the compound (A) contained in Reaction Product a-1 had a structure as shown in Table 1.

Synthesis Example-2: Synthesis of Reaction Product a-2

Reaction Produce a-2 was obtained in the same manner as in Synthesis Example-1 except that diethyl sulfate was used instead of dimethyl sulfate. Reaction Product a-2 was a mixture containing the compounds (A1), (A2), (A3) and (A4) in a ratio indicated in Table 1. Further, the compound (A) contained in Reaction Product a-2 had a structure as shown in Table 1.

Synthesis Example-3: Synthesis of Reaction Product a-3

Reaction Produce a-3 was obtained in the same manner as in Synthesis Example-1 except that caprylic acid was used instead of capric acid. Reaction Product a-3 was a mixture containing the compounds (A1), (A2), (A3) and (A4) in a ratio indicated in Table 1. Further, the compound (A) contained in Reaction Product a-3 had a structure as shown in Table 1.

Synthesis Example-4: Synthesis of Reaction Product a-4

Into a four-necked flask with a volume of 1 L, 254.6 g of capric acid and 371.2 g of triethanolamine (molar ratio of capric acid/triethanolamine=0.6/1) were fed, and reacted with each other for 1 hour under conditions at 140° C. and normal pressure, and then subjected to dehydration-condensation reaction for 2 hours at 180° C. under a reduced pressure of 220 hPa, so that ester amine was obtained. 199.9 g of the obtained ester amine and 40.1 g of methyl chloride were used and reacted with each other in an autoclave for 3 hours at 60° C. by stirring, and then, nitrogen was introduced at 6 L/hr·kg at 60° C. and 25 kPa with 1-hour stirring to distill off unreacted methyl chloride, so that Reaction Product a-4 was obtained. Reaction Product a-4 was a mixture containing the compounds (A1), (A2), (A3) and (A4) in a ratio indicated in Table 1. Further, the compound (A) contained in Reaction Product a-4 had a structure as shown in Table 1.

Synthesis Example-5: Synthesis of Reaction Product a-5

Reaction Product a-5 was obtained in the same manner as in Synthesis Example-1 except that the molar ratio between capric acid and triethanolamine was 0.8/1 of capric acid/triethanolamine. Reaction Product a-5 was a mixture containing the compounds (A1), (A2), (A3) and (A4) in a ratio indicated in Table 1. Further, the compound (A) contained in Reaction Product a-5 had a structure as shown in Table 1.

Synthesis Example-6: Synthesis of Reaction Product a-6

Reaction Product a-6 was obtained in the same manner as in Synthesis Example-1 except that the molar ratio between capric acid and triethanolamine was 1/1 of capric acid/triethanolamine. Reaction Product a-6 was a mixture containing the compounds (A1), (A2), (A3) and (A4) in a ratio indicated in Table 1. Further, the compound (A) contained in Reaction Product a-6 had a structure as shown in Table 1.

Synthesis Example-7: Synthesis of Reaction Product a-7

Reaction Product a-7 was obtained in the same manner as in Synthesis Example-1 except that lauric acid was used instead of capric acid. Reaction Product a-7 was a mixture containing the compounds (A1), (A2), (A3) and (A4) in a ratio indicated in Table 1. Further, the compound (A) contained in Reaction Product a-7 had a structure as shown in Table 1.

Comparative Synthesis Example-1: Synthesis of Comparative Reaction Product-1

Comparative Reaction Product-1 was obtained in the same manner as in Synthesis Example-1 except that capric acid and triethanolamine were used in a molar ratio of 1.2/1. Comparative Reaction Product-1 was a mixture containing the compounds (A1), (A2), (A3) and (A4) in a ratio indicated in Table 1. Further, the compound (A) contained in Comparative Reaction Product-1 had a structure as shown in Table 1.

Comparative Synthesis Example-2: Synthesis of Comparative Reaction Product-2

Into an autoclave, 100 g of triethanolamine, 99 g of lauric acid, and 0.7 kg of 48%-potassium hydroxide aqueous solution were fed. Conditions inside the autoclave were 100° C. and 4.0 kPa (30 torr), and under such conditions, dehydration reaction was caused for 1 hour. Next, the temperature was increased to 150° C., and 259 g of ethylene oxide was introduced into the autoclave at that temperature, thereby causing an addition reaction. After the end of the reaction, the obtained reaction mixture was placed into a treatment tank. Then, 7 g of an alkali adsorbent (KYO-WAAD 600s) was added to the reaction mixture, and the obtained mixture was stirred for 1 hour at 80° C. and 4.0 kPa (30 torr). The obtained reaction mixture was filtrated and a filtrate was obtained as a product. 183.7 g of this product and 40.1 g of methyl chloride were used and reacted with each other in an autoclave at 60° C. by 3-hour stirring, then, stirred for 1 hour while nitrogen was introduced at 6 L/hr·kg at 60° C. and 25 kPa to distill off unreacted methyl chloride, and quaternized, so that Comparative Reaction Product-2 was obtained.

Comparative Reaction Product-2 was a mixture of:

(I) a compound, wherein, in the following formula (1'), $R^1$ is a methyl group, $Y^1$ is —CO—$R^2$ ($R^2$ is a linear alkyl group with 11 carbon atoms), $Y^2$ and $Y^3$ are each a hydrogen atom, p+q+r is 15, and $X^-$ is a chloride ion (monoester-type compound, referred to as compound (A1') for convenience);

(II) a compound, wherein, in the following formula (1'), $R^1$ is a methyl group, $Y^1$ and $Y^2$ are each —CO—$R^2$ ($R^2$ is a linear alkyl group with 11 carbon atoms), $Y^3$ is a hydrogen atom, p+q+r is 15, and $X^-$ is a chloride ion (diester-type compound, referred to as compound (A2') for convenience);

(III) a compound, wherein, in the following formula (1'), $R^1$ is a methyl group, $Y^1$, $Y^2$ and $Y^3$ are each —CO—$R^2$ ($R^2$ is a linear alkyl group with 11 carbon atoms), p+q+r is 15, and $X^-$ is a chloride ion (triester-type compound, referred to as compound (A3') for convenience); and (IV) a compound, wherein, in the following formula (1'), $R^1$ is a methyl group, $Y^1$, $Y^2$ and $Y^3$ are each a hydrogen atom, p+q+r is 15, and $X^-$ is a chloride ion (quaternized triethanolamine, referred to as compound (A4') for convenience), and the ratios thereof were as shown in Table 1.

[Chemical Formula 18]

$$R^1-\overset{+}{N}\begin{pmatrix}(CH_2CH_2O)_p-Y^1\\(CH_2CH_2O)_q-Y^2\\(CH_2CH_2O)_r-Y^3\end{pmatrix}\quad X^- \qquad (1')$$

Comparative Synthesis Example-3: Synthesis of Comparative Reaction Product-3

68.6 g of triethanolamine and 54.9 g of dimethyl sulfate were used and quaternized, so that Comparative Reaction Product-3 was obtained. Synthesis was conducted in the same manner as quaternization (latter half of the experiment) of Synthesis Example-1 except that triethanolamine was directly used instead of the ester amine obtained by dehydration-condensation reaction. The obtained Comparative Reaction Product-3 contained none of the compounds (A1), (A2) and (A3), and it was substantially compound (A4) itself as shown in Table 1.

<Preparation of Efficacy-Enhancing Agent Compositions for Agrochemicals>

The compounds (A), (A'), (B) and (C), and water were weighed based on the composition shown in Table 2 so that an efficacy-enhancing agent composition for agrochemicals had a total mass of 50 g, and stirred and mixed for 10 minutes by a stirrer, so that the efficacy-enhancing agent composition for agrochemicals was obtained.

<Preparation of Agrochemical Compositions>

The efficacy-enhancing agent composition for agrochemicals, an agrochemical active ingredient (D), water and a solvent were weighed based on the composition shown in Table 2 so that an agrochemical composition had a total mass of 100 g, and stirred and mixed for 10 minutes by a stirrer, so that the agrochemical composition was obtained.

Components used in Examples and Comparative Examples are indicated below.

<Compound (A): Indicated as (A) in Table 2>

Compound a-1: Reaction Product a-1 obtained in Synthesis Example-1

Compound a-2: Reaction Product a-2 obtained in Synthesis Example-2

Compound a-3: Reaction Product a-3 obtained in Synthesis Example-3

Compound a-4: Reaction Product a-4 obtained in Synthesis Example-4

Compound a-5: Reaction Product a-5 obtained in Synthesis Example-5

Compound a-6: Reaction Product a-6 obtained in Synthesis Example-6

Compound a-7: Reaction Product a-7 obtained in Synthesis Example-7

<Comparative Compound of Compound (A): Indicated as (A') in Table 2>

Comparative Compound-1: Comparative Reaction Product-1 obtained in Comparative Synthesis Example-1

Comparative Compound-2: Comparative Reaction Product-2 obtained in Comparative Synthesis Example-2

Comparative Compound-3: Comparative Reaction Product-3 obtained in Comparative Synthesis Example-3

Comparative Compound-4: polyoxyethylene stearyl amine (average addition molar number of ethyleneoxide=20) (manufactured by Kao Corporation: AMIET 320)

<Compound (B): Indicated as (B) in Table 2>
b-1: polyoxyethylene lauryl ether (average addition molar number of ethyleneoxide=6) (manufactured by Kao Corporation: Emulgen 108)
<Compound (C): Indicated as (C) in Table 2>
c-1: polyoxypropylene octyl ether (average addition molar number of propyleneoxide=3)
c-2: decyl alcohol (manufactured by Kao Corporation: KALCOL 1098)
<Amino Acid-Based Agrochemical Active Ingredient (D): Indicated as (D) in Table 2>
d-1: glyphosate isopropyl amine salt
d-2: glyphosate potassium salt
d-3: glufosinate ammonium salt
<Evaluation>
[Biodegradability of Compound (A) or Comparative Compound of Compound (A)]

In accordance with the same method as the 301C method of OECD (Organization for Economic Co-operation and Development) test guidelines, biodegradability tests were conducted on the compound (A) or the comparative compound [compound (A')] of the compound (A). In terms of the BOD, one having 60% or more was evaluated as "Good," one having 30% or more and less than 60% as "Fair" and one having less than 30% as "Poor."
[Fish Toxicity of Compound (A) or Comparative Compound of Compound (A)]

In accordance with the same method as the TG203 method of OECD (Organization for Economic Co-operation and Development) test guidelines, fish toxicity tests were conducted on the compound (A) or the comparative compound [compound (A')] of the compound (A). In terms of LC50, one having 1 mg or more was evaluated as "Good," one having less than 1 mg as "Poor." It is prescribed that a product having an LC50 of less than 1 mg should have a symbol mark on a GHS label indication.
[Formulation Stability of Agrochemical Compositions]

40 g of an agrochemical composition just after preparation was placed in a transparent glass container (volume: 50 ml); and when it is stored at 60° C., the number of days, during which it can maintain a transparent and homogeneous appearance, was evaluated.
5: transparence and homogeneity were maintained for 10 days or more
4: transparence and homogeneity were maintained for 8 to 9 days
3: transparence and homogeneity were maintained for 3 to 7 days
2: transparence and homogeneity were maintained for 1 to 2 days
1: separation or precipitation occurred within less than 1 day
[Herbicidal Property Test]

A barnyard grass was grown in a 12 cm-pot, and a plant body thereof having a height of about 30 cm was used for the test. An agrochemical composition having a composition shown in the table was prepared and diluted with water by 185 times, so that an agrochemical spray solution was obtained. This agrochemical spray solution was used for foliar spray so as to be applied on the entire of a plant body at an application amount of 500 L/ha, and then an herbicidal efficacy was evaluated. For the evaluation of the herbicidal efficacy, a mass of above-ground part was measured on 14th day after the spraying, and an herbicidal rate was calculated based on the following equation using a mass of above-ground part in a non-treated area as a reference. A higher numeral value of the herbicidal rate indicates a higher agrochemical efficacy (herbicidal effect). The term "non-treated area" used herein is an area where a diluted mixture (agrochemical spray solution) of an agrochemical and an efficacy-enhancing agent composition for agrochemicals was not sprayed (the same is applied to other tests).

Herbicidal rate (%)=(mass of above-ground part in non-treated area−mass of above-ground part in treated area)/mass of above-ground part in non-treated area×100

One having an herbicidal rate of less than 80% is at such a level that an herbicidal effect cannot be expected.

Further, no herbicidal property test was conducted on one having an evaluation score of 1 in the formulation stability test.
[Rain Resistance Test]

A barnyard grass was grown in a 12 cm-pot. Among leaves of plant bodies having a height of about 30 cm, one leaf with a leaf length of 20±1 cm was placed on a horizontal table without being separated from a plant body, and a tip and a bottom of the leaf were fixed so that the front of the foliar surface was shown. On the foliar surface of the fixed leaf, 5 μL of a liquid prepared by diluting an agrochemical composition having a composition shown in the table with water by 16.8 times was dropped by a syringe at 5 equally spaced locations. After the dropping, the leaf was left to stand for 1.5 hours, and then an amount of water equivalent to a rainfall intensity of 30 mm/h was sprayed on the foliar surface for 10 minutes. Thereafter, a stem of the plant body was cut at 20 mm above the ground and an upper part was removed. A height of a regrown part of the plant body on the 21st day after the cutting was calculated as a regrown plant height by the following equation. A smaller regrown height exhibits a higher rain resistance.

One exhibiting a higher rain resistance in this test enables an extension of a spraying interval of an agrochemical (reduction of the spraying frequency) and avoidance of weeding effect dissipation caused by rainfall or the like after spraying of an agrochemical.

Regrown plant height (mm)=Height (mm) of plant body on the 21st day after cutting−20

TABLE 1

| | Structures in general formulas (1-1) to (1-4) | | | Composition (% by mass) Compound | | | | | Composition (mass ratio) | | | | | |
|---|---|---|---|---|---|---|---|---|---|---|---|---|---|---|
| | | | | | | | | | Mass ratio to (A1) + (A2) + (A3) | | | (A3)/ [(A1) + (A2)] | (A4)/ (A1) | (A4)/ [(A1) + (A2)] |
| Symbol | $R^1$ | $R^2$ | $X^-$ | (A1) | (A2) | (A3) | (A4) | Other | (A1) | (A2) | (A3) | | | |
| Compound a-1 | Methyl group | $C_9$ linear alkyl group | Methyl sulfate anion | 52 | 20 | 3 | 24 | 1 | 69 | 27 | 4 | 4/96 | 28/72 | 25/75 |
| Compound a-2 | Ethyl group | $C_9$ linear alkyl group | Ethyl sulfate anion | 51 | 20 | 3 | 25 | 1 | 69 | 27 | 4 | 4/96 | 28/72 | 26/74 |

TABLE 1-continued

| | Structures in general formulas (1-1) to (1-4) | | | Composition (% by mass) Compound | | | | | Composition (mass ratio) | | | | | |
|---|---|---|---|---|---|---|---|---|---|---|---|---|---|---|
| | | | | | | | | | Mass ratio to (A1) + (A2) + (A3) | | | (A3)/ [(A1) + (A2)] | (A2)/ (A1) | (A4)/ [(A1) + (A2)] |
| Symbol | $R^1$ | $R^2$ | $X^-$ | (A1) | (A2) | (A3) | (A4) | Other | (A1) | (A2) | (A3) | | | |
| Compound a-3 | Methyl group | $C_7$ linear alkyl group | Methyl sulfate anion | 51 | 21 | 3 | 24 | 1 | 68 | 28 | 4 | 4/96 | 29/71 | 25/75 |
| Compound a-4 | Methyl group | $C_9$ linear alkyl group | Chloride ion | 51 | 21 | 3 | 24 | 1 | 69 | 27 | 4 | 4/96 | 29/71 | 25/75 |
| Compound a-5 | Methyl group | $C_9$ linear alkyl group | Methyl sulfate anion | 49 | 29 | 5 | 16 | 1 | 59 | 35 | 6 | 6/94 | 37/63 | 17/83 |
| Compound a-6 | Methyl group | $C_9$ linear alkyl group | Methyl sulfate anion | 45 | 35 | 8 | 11 | 1 | 51 | 40 | 9 | 9/91 | 44/56 | 12/88 |
| Compound a-7 | Methyl group | $C_{11}$ linear alkyl group | Methyl sulfate anion | 52 | 21 | 3 | 23 | 1 | 68 | 28 | 4 | 4/96 | 29/71 | 24/76 |
| Comparative Compound-1 | Methyl group | $C_9$ linear alkyl group | Methyl sulfate anion | 37 | 41 | 13 | 8 | 1 | 41 | 45 | 14 | 14/86 | 53/47 | 9.3/90.7 |
| Comparative Compound-2 | Methyl group | $C_{11}$ linear alkyl group | Chloride ion | 56*[1] | 16*[2] | 8*[3] | 19*[4] | 1 | 70 | 20 | 10 | 10/90 | 22/78 | 21/79 |
| Comparative Compound-3 | Methyl group | — | Methyl sulfate anion | 0 | 0 | 0 | 99 | 1 | — | — | — | — | — | — |

*[1]Ratio of compound (A1') of Comparative Compound-2
*[2]Ratio of compound (A2') of Comparative Compound-2
*[3]Ratio of compound (A3') of Comparative Compound-2
*[4]Ratio of compound (A4') of Comparative Compound-2

TABLE 2

| | | | | | Examples | | | | | | | | | |
|---|---|---|---|---|---|---|---|---|---|---|---|---|---|---|
| | | | | | 1 | 2 | 3 | 4 | 5 | 6 | 7 | 8 | 9 | 10 |
| Agrochemical composition | Formulation components (% by mass) | Efficacy-enhancing agent composition for agro-chemicals | (A) | Compound a-1 | 7.5 | | | | | | | 7.5 | 7.5 | 7.5 |
| | | | | Compound a-2 | | 7.5 | | | | | | | | |
| | | | | Compound a-3 | | | 7.5 | | | | | | | |
| | | | | Compound a-4 | | | | 7.5 | | | | | | |
| | | | | Compound a-5 | | | | | 7.5 | | | | | |
| | | | | Compound a-6 | | | | | | 7.5 | | | | |
| | | | | Compound a-7 | | | | | | | 7.5 | | | |
| | | | (A') | Comparative Compound-1 | | | | | | | | | | |
| | | | | Comparative Compound-2 | | | | | | | | | | |
| | | | | Comparative Compound-3 | | | | | | | | | | |
| | | | | Comparative Compound-4 | | | | | | | | | | |
| | | | (B) | b-1 | | | | | | | | 1.5 | | |
| | | | (C) | c-1 | | | | | | | | | 1.5 | |
| | | | | c-2 | | | | | | | | | | 1.5 |
| | | | | Water | 4 | 4 | 4 | 4 | 4 | 4 | 4 | 4 | 4 | 4 |
| | | Agrochemical active ingredient | (D) | d-1 | 41 | 41 | 41 | 41 | 41 | 41 | 41 | 41 | 41 | 41 |
| | | | | d-2 | | | | | | | | | | |
| | | | | d-3 | | | | | | | | | | |
| | | Solvent (propylene glycol monomethyl ether) | | | | | | | | | | | | |
| | | Water | | | Balance | Balance | Balance | Balance | Balance | Balance | Balance | Balance | Balance | Balance |
| | Total | | | | 100 | 100 | 100 | 100 | 100 | 100 | 100 | 100 | 100 | 100 |
| | Content of compound (A1) (% by mass) | | | | 3.9 | 3.8 | 3.8 | 3.8 | 3.7 | 3.4 | 3.9 | 3.9 | 3.9 | 3.9 |
| | Content of compound (A2) (% by mass) | | | | 1.5 | 1.5 | 1.6 | 1.6 | 2.2 | 2.6 | 1.6 | 1.5 | 1.5 | 1.5 |
| | Content of compound (A3) (% by mass) | | | | 0.2 | 0.2 | 0.2 | 0.2 | 0.4 | 0.6 | 0.2 | 0.2 | 0.2 | 0.2 |
| | Content of compound (A4) (% by mass) | | | | 1.8 | 1.9 | 1.8 | 1.8 | 1.2 | 0.8 | 1.8 | 1.8 | 1.8 | 1.8 |
| | Total of [(A) or (A')] + (B) + (C) (% by mass) | | | | 7.5 | 7.5 | 7.5 | 7.5 | 7.5 | 7.5 | 7.5 | 9 | 9 | 9 |

TABLE 2-continued

|  |  |  |  |  |  |  |  |  | 5/1 | 5/1 | 5/1 |
|---|---|---|---|---|---|---|---|---|---|---|---|
| [(A) or (A')]/[(B) + (C)] (mass ratio) |  |  |  |  |  |  |  |  |  |  |  |
| (B)/(C) (mass ratio) | — | — | — | — | — | — | — | 0 | 0 |
| Total content of water | 51.5 | 51.5 | 51.5 | 51.5 | 51.5 | 51.5 | 51.5 | 50 | 50 | 50 |
| Biodegradabiltiy of (A) or (A') | Good | Good | Good | Good | Good | Good | Good | Good | Good | Good |
| Fish toxicity of (A) or (A') | Good | Good | Good | Good | Good | Good | Good | Good | Good | Good |
| Formulation stability of agrochemical composition | 5 | 5 | 5 | 5 | 5 | 5 | 5 | 5 | 4 | 4 |
| Herbicidal rate (%) | 93 | 92 | 90 | 91 | 92 | 91 | 91 | 95 | 96 | 94 |
| Regrown plant height (mm) | 24 | 29 | 28 | 27 | 27 | 29 | 28 | 19 | 18 | 18 |

|  |  |  |  |  | Examples | | | Comparative Examples | | | | | | |
|---|---|---|---|---|---|---|---|---|---|---|---|---|---|---|
|  |  |  |  |  | 11 | 12 | 13 | 1 | 2 | 3 | 4 | 5 | 6 | 7 |
| Agro-chemical composition | Formu-lation compo-nents (% by mass) | Efficacy-enhancing agent composi-tion for agro-chemicals | (A) | Compound a-1 | 7.5 | 7.5 | 10 |  |  |  |  |  |  |  |
|  |  |  |  | Compound a-2 |  |  |  |  |  |  |  |  |  |  |
|  |  |  |  | Compound a-3 |  |  |  |  |  |  |  |  |  |  |
|  |  |  |  | Compound a-4 |  |  |  |  |  |  |  |  |  |  |
|  |  |  |  | Compound a-5 |  |  |  |  |  |  |  |  |  |  |
|  |  |  |  | Compound a-6 |  |  |  |  |  |  |  |  |  |  |
|  |  |  |  | Compound a-7 |  |  |  |  |  |  |  |  |  |  |
|  |  |  | (A') | Comparative Compound-1 |  |  |  | 7.5 |  |  |  |  |  |  |
|  |  |  |  | Comparative Compound-2 |  |  |  |  | 7.5 | 7.5 | 7.5 | 10 |  |  |
|  |  |  |  | Comparative Compound-3 |  |  |  |  |  |  |  |  | 7.5 |  |
|  |  |  |  | Comparative Compound-4 |  |  |  |  |  |  |  |  |  | 7.5 |
|  |  |  | (B) | b-1 | 0.75 |  |  |  |  | 0.75 |  |  |  |  |
|  |  |  | (C) | c-1 | 0.75 |  |  |  |  | 0.75 |  |  |  |  |
|  |  |  |  | c-2 |  |  |  |  |  |  |  |  |  |  |
|  |  |  | Water |  | 4 | 4 | 4 | 4 | 4 | 4 | 4 | 4 | 4 | 4 |
|  |  | Agro-chemical active ingredient | (D) | d-1 | 41 |  |  | 41 | 41 | 41 |  |  | 41 | 41 |
|  |  |  |  | d-2 |  | 41 |  |  |  |  | 41 |  |  |  |
|  |  |  |  | d-3 |  |  | 20 |  |  |  |  | 20 |  |  |
|  |  | Solvent (propylene glycol monomethyl ether) |  |  |  |  | 10 |  |  |  |  | 10 |  |  |
|  |  | Water |  |  | Balance | Balance | Balance | Balance | Balance | Balance | Balance | Balance | Balance | Balance |
|  |  | Total |  |  | 100 | 100 | 100 | 100 | 100 | 100 | 100 | 100 | 100 | 100 |
| Content of compound (A1) (% by mass) |  |  |  |  | 3.9 | 3.9 | 5.2 | 2.8 | 0 | 0 | 0 | 0 | 0 | 0 |
| Content of compound (A2) (% by mass) |  |  |  |  | 1.5 | 1.5 | 2.0 | 3.1 | 0 | 0 | 0 | 0 | 0 | 0 |
| Content of compound (A3) (% by mass) |  |  |  |  | 0.2 | 0.2 | 0.3 | 1.0 | 0 | 0 | 0 | 0 | 0 | 0 |

TABLE 2-continued

| Content of compound (A4) (% by mass) | 1.8 | 1.8 | 2.4 | 0.6 | 0 | 0 | 0 | 0 | 7.4 | 0 |
|---|---|---|---|---|---|---|---|---|---|---|
| Total of [(A) or (A')] + (B) + (C) (% by mass) | 9 | 7.5 | 10 | 7.5 | 7.5 | 9 | 7.5 | 10 | 7.5 | 7.5 |
| [(A) or (A')]/[(B) + (C)] (mass ratio) | 5/1 | — | — | — | — | 5/1 | — | — | — | — |
| (B)/(C) (mass ratio) | 1/1 | — | — | — | — | 1/1 | — | — | — | — |
| Total content of water | 50 | 51.5 | 60 | 51.5 | 51.5 | 50 | 51.5 | 60 | 51.5 | 51.5 |
| Biodegradabiltiy of (A) or (A') | Good | Good | Good | Good | Good | Good | Good | Good | Poor | Poor |
| Fish toxicity of (A) or (A') | Good | Good | Good | Good | Good | Good | Good | Good | Good | Poor |
| Formulation stability of agrochemical composition | 5 | 5 | 4 | 4 | 4 | 1 | 4 | 4 | 5 | 5 |
| Herbicidal rate (%) | 99 | 91 | 91 | 75 | 71 | — | 67 | 63 | 53 | 90 |
| Regrown plant height (mm) | 15 | 22 | 35 | 65 | 70 | — | 75 | 185 | 193 | 138 |

In Table 2, (A') is regarded as (A) for convenience, and the total of (A)+(B)+(C) and (A)/[(B)+(C)] are indicated.

In Table 2, the symbol "-" in the herbicidal rate and the regrown plant height signifies that evaluations therefor were not conducted since a separation occurred in the agrochemical composition.

It should be noted that Table 3 shows detailed compositions of efficacy-enhancing agent compositions for agrochemicals of Examples. In Table 3, "other" compounds are included in compound (A) for convenience.

TABLE 3

|  |  |  |  | Examples |||||||||||||
|---|---|---|---|---|---|---|---|---|---|---|---|---|---|---|---|---|
|  |  |  |  | 1 | 2 | 3 | 4 | 5 | 6 | 7 | 8 | 9 | 10 | 11 | 12 | 13 |
| Efficacy-enhancing agent composition for agrochemicals | Formulation components (% by mass) | Compound(A) | Compound(A1) | 33.91 | 33.26 | 33.26 | 33.26 | 31.96 | 29.35 | 33.90 | 30.00 | 30.00 | 30.00 | 30.00 | 33.91 | 37.14 |
|  |  |  | Compound(A2) | 13.04 | 13.04 | 13.69 | 13.69 | 18.91 | 22.82 | 13.69 | 11.54 | 11.54 | 11.54 | 11.54 | 13.04 | 14.29 |
|  |  |  | Compound(A3) | 1.96 | 1.96 | 1.96 | 1.96 | 3.26 | 5.22 | 1.96 | 1.73 | 1.73 | 1.73 | 1.73 | 1.96 | 2.14 |
|  |  |  | Compound(A4) | 15.65 | 16.30 | 15.65 | 15.65 | 10.43 | 7.17 | 15.00 | 13.85 | 13.85 | 13.85 | 13.85 | 15.65 | 17.14 |
|  |  |  | Other | 0.65 | 0.65 | 0.65 | 0.65 | 0.65 | 0.65 | 0.65 | 0.58 | 0.58 | 0.58 | 0.58 | 0.65 | 0.71 |
|  |  | Compound(B) | b-1 |  |  |  |  |  |  |  | 11.54 |  |  | 5.77 |  |  |
|  |  | Compound(C) | c-1 |  |  |  |  |  |  |  |  | 11.54 |  | 5.77 |  |  |
|  |  |  | c-2 |  |  |  |  |  |  |  |  |  | 11.54 |  |  |  |
|  |  | Water |  | 34.79 | 34.79 | 34.79 | 34.79 | 34.79 | 34.79 | 34.80 | 30.76 | 30.76 | 30.76 | 30.76 | 34.79 | 28.58 |
|  | (A1)/(B) (mass ratio) |  |  | — | — | — | — | — | — | — | 2.6/1 | — | — | 5.2/1 | — | — |
|  | (A1)/(C) (mass ratio) |  |  | — | — | — | — | — | — | — | — | 2.6/1 | 2.6/1 | 5.2/1 | — | — |
|  | (A1)/[(B) + (C)](mass ratio) |  |  | — | — | — | — | — | — | — | 2.6/1 | 2.6/1 | 2.6/1 | 2.6/1 | — | — |
|  | (B)/(C) (mass ratio) |  |  | — | — | — | — | — | — | — | — | 0 | 0 | 1/1 | — | — |

The invention claimed is:

1. An efficacy-enhancing agent composition for amino acid-based agrochemicals, comprising a compound (A1) represented by the following general formula (1-1), optionally a compound (A2) represented by the following general formula (1-2), and optionally a compound (A3) represented by the following general formula (1-3), wherein:

the mass ratio of the content of the compound (A3) to the sum of the contents of the compound (A1) and the compound (A2), [content of compound (A3)]/[sum of contents of compounds (A1) and (A2)], is 0/100 or more and 10/90 or less; and the mass ratio of the content of the compound (A2) to the content of the compound (A1), [content of compound (A2)]/[content of compound (A1)], is 0/100 or more and 50/50 or less,

[Chemical Formula 1]

$$R^1 - \overset{+}{N} \begin{array}{l} CH_2CH_2 - O - \overset{O}{\overset{\|}{C}} - R^2 \\ CH_2CH_2 - O - H \\ CH_2CH_2 - O - H \end{array} \quad X^- \tag{1-1}$$

[Chemical Formula 2]

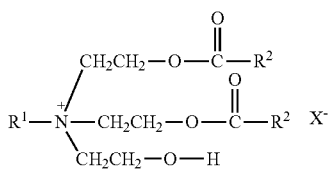

(1-2)

[Chemical Formula 3]

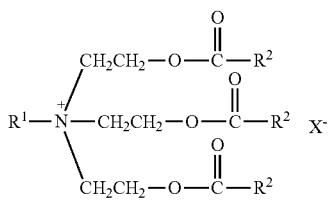

(1-3)

in the formulas, $R^1$ denotes a linear alkyl group having 1 or more and 4 or less carbon atoms, a linear alkenyl group having 2 or more and 4 or less carbon atoms, a branched alkyl group having 3 or more and 4 or less carbon atoms, or a branched alkenyl group having 3 or more and 4 or less carbon atoms; $R^2$ denotes a linear or branched alkyl or alkenyl group having 5 or more and 11 or less carbon atoms; and $X^-$ denotes a counter ion.

2. The efficacy-enhancing agent composition for amino acid-based agrochemicals according to claim 1, wherein the compound (A1) is a compound of the general formula (1-1) in which $R^1$ is a linear alkyl group with 1 or more and 2 or less carbon atoms.

3. The efficacy-enhancing agent composition for amino acid-based agrochemicals according to claim 1, wherein the compound (A1) is a compound of the general formula (1-1) in which $R^2$ is a linear alkyl group with 7 or more and 11 or less carbon atoms.

4. The efficacy-enhancing agent composition for amino acid-based agrochemicals according to claim 1, wherein the compound (A1) is a compound of the general formula (1-1) in which $X^-$ is a halogenide ion or an alkyl sulfate anion.

5. An agrochemical composition comprising an efficacy-enhancing agent composition for amino acid-based agrochemicals of claim 1, an amino acid-based agrochemical active ingredient (D), and water.

6. The agrochemical composition according to claim 5, wherein the amino acid-based agrochemical active ingredient (D) is at least one compound selected from N-(phosphonomethyl)glycine or salts thereof, and ammonium DL-homoalanine-4-yl(methyl)phosphinate.

7. The agrochemical composition according to claim 6, wherein the amino acid-based agrochemical active ingredient (D) is N-(phosphonomethyl)glycine or a salt thereof.

8. A method for weeding comprising spraying on a plant an agrochemical spray solution prepared from an agrochemical composition of claim 5.

9. A method for enhancing an efficacy of an amino acid-based agrochemical, comprising:
combining the efficacy-enhancing agent composition for amino acid-based agrochemicals of claim 1 with the amino acid-based agrochemical.

10. A method for producing an agrochemical composition, comprising mixing an efficacy-enhancing agent composition for amino acid-based agrochemicals of claim 1, an amino acid-based agrochemical active ingredient (D), and water.

* * * * *